(12) United States Patent
Jun et al.

(10) Patent No.: US 10,470,620 B2
(45) Date of Patent: Nov. 12, 2019

(54) BATHROOM MANAGEMENT APPARATUS

(71) Applicant: LG ELECTRONICS INC., Seoul (KR)

(72) Inventors: Wheeyoung Jun, Seoul (KR); Daeyun Park, Seoul (KR); Minjung Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 244 days.

(21) Appl. No.: 15/693,703

(22) Filed: Sep. 1, 2017

(65) Prior Publication Data

US 2018/0064296 A1 Mar. 8, 2018

(30) Foreign Application Priority Data

Sep. 2, 2016 (KR) .................. 10-2016-0113359

(51) Int. Cl.
| | |
|---|---|
| *A47K 10/06* | (2006.01) |
| *F26B 21/00* | (2006.01) |
| *F26B 9/00* | (2006.01) |
| *F26B 25/22* | (2006.01) |
| *A61L 2/14* | (2006.01) |

(Continued)

(52) U.S. Cl.
CPC .............. *A47K 10/06* (2013.01); *A61L 2/10* (2013.01); *A61L 2/14* (2013.01); *A61L 2/24* (2013.01); *A61L 9/18* (2013.01); *A61L 9/205* (2013.01); *F26B 9/003* (2013.01); *F26B 21/003* (2013.01); *F26B 23/06* (2013.01); *F26B 25/22* (2013.01); *A61L 2202/11* (2013.01); *A61L 2202/14* (2013.01); *A61L 2202/15* (2013.01); *A61L 2202/26* (2013.01); *A61L 2209/12* (2013.01); *A61L 2209/14* (2013.01)

(58) Field of Classification Search
CPC .......... F26B 23/06; F26B 25/22; F26B 9/003; F26B 21/003; A47K 10/06; A61L 9/205; A61L 2/10; A61L 2/24; A61L 2/14; A61L 9/18; A61L 2209/14; A61L 2202/15; A61L 2202/14; A61L 2202/11; A61L 2209/12; A61L 2202/26
See application file for complete search history.

(56) References Cited

U.S. PATENT DOCUMENTS

| | | | | |
|---|---|---|---|---|
| 5,548,100 A | * | 8/1996 | Miller .................... | A47K 10/06 219/385 |
| 6,153,862 A | * | 11/2000 | Job ........................ | A47K 10/06 219/385 |

(Continued)

*Primary Examiner* — Jessica Yuen
(74) *Attorney, Agent, or Firm* — KED & Associates, LLP

(57) ABSTRACT

A bathroom management apparatus includes a case including a air discharge port for the discharge of air, a discharge vane for opening and closing the air discharge port, and a hanger coupled to the case and including a hanger part, wherein a front end of the discharge vane is positioned behind and under the air discharge port when the air discharge port is opened, wherein the hanger part is positioned between a first tangential line and a first straight line, which define a predetermined angle with respect to each other, and wherein the predetermined angle is an angle between a second tangential line extending along a rear inner surface of the second air discharge port and a second straight line extending through a lower rear end of the second air discharge port and a front end of the opened discharge vane.

20 Claims, 29 Drawing Sheets

(51) Int. Cl.
*A61L 2/24* (2006.01)
*A61L 2/10* (2006.01)
*A61L 9/18* (2006.01)
*F26B 23/06* (2006.01)
*A61L 9/20* (2006.01)

(56) References Cited

U.S. PATENT DOCUMENTS

| | | | |
|---|---|---|---|
| 7,597,122 B1 * | 10/2009 | Smith | A47K 5/1202 |
| | | | 141/114 |
| 8,166,667 B1 * | 5/2012 | Lora | F26B 9/003 |
| | | | 34/202 |
| 10,240,806 B2 * | 3/2019 | Lee | F24F 13/1413 |
| 2018/0066867 A1 * | 3/2018 | Kim | A61L 2/06 |

* cited by examiner

BATHROOM MANAGEMENT APPARATUS

CROSS-REFERENCE TO RELATED APPLICATIONS

This application claims priority under 35 U.S.C. §119 to Korean Application No. 10-2016-0113359, filed on Sep. 2, 2016, whose entire disclosure is hereby incorporated by reference.

BACKGROUND

1. Field

The present disclosure relates to an apparatus capable of performing dehumidification and sterilization of a bathroom or other room.

2. Background

Various mold and bacteria may grow in humid sites, such as a laundry or bathroom, and unpleasant odors may be generated. Although drying and deodorization in most bathrooms may be carried out by a ventilation fan, mold and bacteria contamination may occur due to remaining humidity because the ventilation fan is not operated appropriately or because the ventilation fan is insufficient to maintain the entire space of the bathroom in a dry state even when the ventilation fan is operated.

Managing moisture in a bathroom may help prevent the creation of a habitat suitable for mold and bacteria by removing moisture from the floor of the bathroom and drying wet objects, such as towels, hanging in the bathroom in a timely manner. Furthermore, mold and bacteria may proliferate in wet towels hanging in the bathroom.

BRIEF DESCRIPTION OF THE DRAWINGS

The embodiments will be described in detail with reference to the following drawings in which like reference numerals refer to like elements wherein.

DETAILED DESCRIPTION

Figure 1:
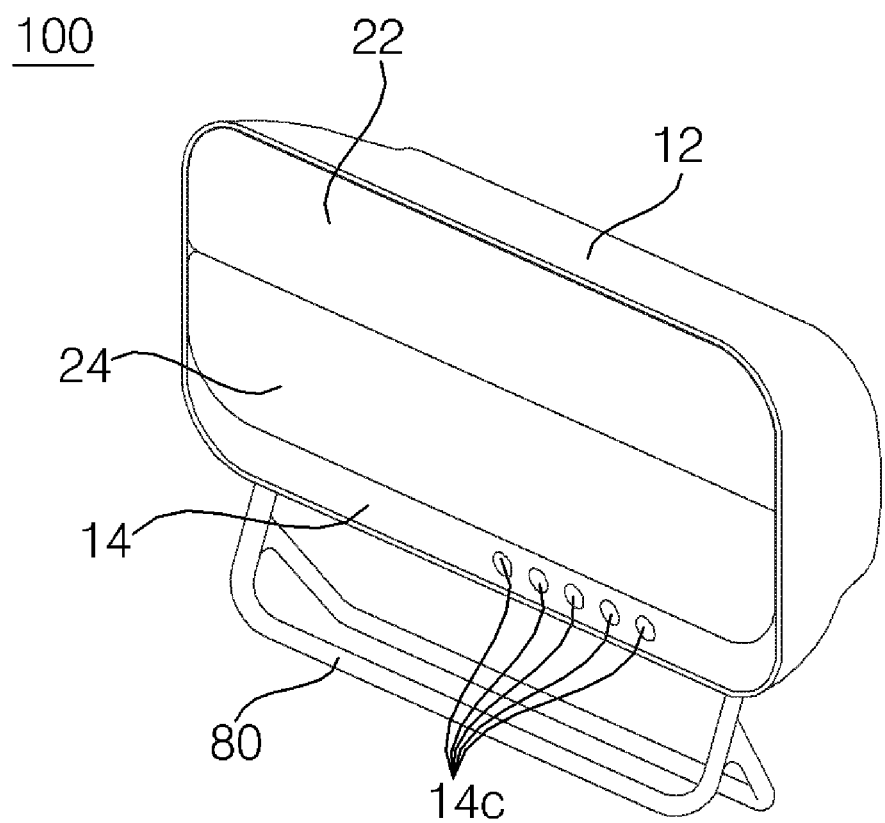
FIG. 1 is a view illustrating a bathroom management apparatus according to an embodiment of the present disclosure.
Figure 2:
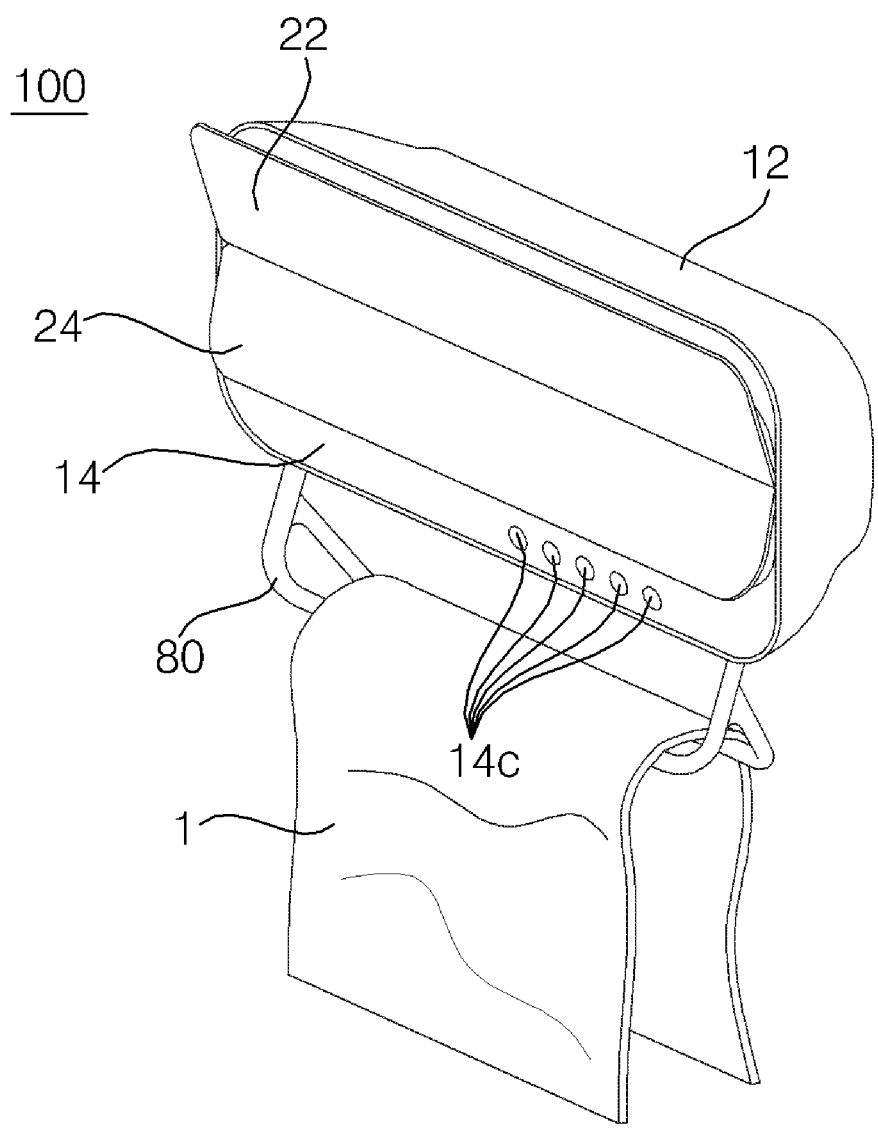
FIG. 2 is a view illustrating an intake vane and a first discharge vane shown in FIG. 1, which are in the open state.

Hereinafter, a bathroom management apparatus (also referred to as a dryer) according to an embodiment of the present disclosure will be described with reference to the accompanying drawings.

Referring to FIGS. 1 to 12, a bathroom management apparatus 100 according to the embodiment of the present disclosure may include a combined case 12 and 14 mounted, for example, on a side wall of a bathroom and defining the appearance of the bathroom management apparatus 100, an intake vane (or intake cover) 30 and a discharge vane (or discharge cover) 24, which are rotatably coupled to the front surface of the combined case 12 and 14, a duct 30 provided in the combined case 12 and 14, a second discharge vane (or discharge cover) 26 rotatably coupled to the duct 30, a blower fan 40 provided in the duct 30 and a heater 50 for heating the air in the duct 30.

The combined case 12 and 14 may include, in an upper region of the front surface thereof, an air intake port 14a that sucks in or receives air from the bathroom and may include, in a lower region of the front surface thereof, a first air discharge port 14b that discharges air heated by the heater 50. The combined case 12 and 14 may further include, in the lower surface thereof, a second air intake port 12a that may also discharge air heated by the heater 50.

The combined case 12 and 14 may include an outer case 12 and an inner case 14. The outer case 12 may be configured to have a hollow hexahedral body, which is open at the front surface thereof. The outer case 12 may include the second air discharge port 12a formed in the lower surface thereof so as to allow the inside of the outer case 12 to communicate with and pass to the outside. The outer case 12 may define the upper surface, the lower surface, the left surface, the right surface and the rear surface of the combined case 12 and 14. In other words, the upper surface of the outer case 12 may correspond to the upper surface of the combined case 12 and 14, and the lower surface of the outer case 12 may correspond to the lower surface of the combined case 12 and 14. Furthermore, the left surface of the outer case 12 may correspond to the left surface of the combined case 12 and 14, the right surface of the outer case 12 may correspond to the right surface of the combined case 12 and 14, and the rear surface of the outer case 12 may correspond to the rear surface of the combined case 12 and 14.

The inner case 14 may be fitted into the outer case 12 through the open front face of the outer case 12. The inner case 14 fitted in the outer case 12 may be provided at a front region of the outer case 12 such that a space for accommodating the duct 30 therein is defined between the rear surface of the outer surface 12 and the inner case 14. The inner case 14 may define the front surface of the combined case 12 and 14. In other words, the inner case 14 may correspond to the front surface of the combined case 12 and 14.

When the intake vane 22 and the first discharge vane 24 are in the closed state, as shown in FIG. 1, the lower end portion of the inner case 14 may be exposed to the outside. The lower end portion of the inner case 14, which is exposed to the outside, may be provided with input buttons 14c, which are pushed by a user. A user may push the input buttons 14c so as to operate the bathroom management apparatus 100 in a desired mode.

The inner case 14 may include an upper part 14d, an intermediate part 14e and a lower part 14f. Accordingly, the upper part 14d of the inner case 14 may correspond to an upper part 14d of the front surface of the combined case 12 and 14, the intermediate part 14e of the inner case 14 may correspond to an intermediate part 14e of the front surface of the combined case 12 and 14, and the lower part 14f of the inner case 14 may correspond to a lower part 14f of the front surface of the combined case 12 and 14. The air intake port 14a may be formed in the upper part 14d of the inner case 14, and the first air discharge port 14b may be formed in the lower part 14f of the inner case 14. The intermediate part 14e may refer to the portion defined between the air intake port 14a and the first air discharge port 14b in the inner case 14.

The upper part 14d of the inner case 14 may be provided with division plates 14g adapted to divide the air intake port 14a into a plurality of port segments. The intermediate part 14e of the inner case 14 may be provided with a lighting device (or lighting source) 15 that emits light. The lighting device 15 may be composed of a lens cover 15a coupled to the inner case 14 and a plurality of light-emitting diodes (LEDs) provided in the lens cover 15a, or the lighting device 15 may include a bulb for emitting light, in place of the plurality of light-emitting diodes. When the intake vane 22 opens the air intake port 14a, the lighting device 15 may be exposed through an upper space defined between the inner case 14 and the intake vane 22. Accordingly, when the lighting device 15 generates light while the intake vane 22 is open to expose the air intake port 14a, the light generated by the lighting device 15 may be radiated into the bathroom through the upper space defined between the inner case 14 and the intake vane 22.

The upper part of the front surface of the inner case 14 may be provided with a filter 60. The filter 60 may be provided in the air intake port 14a so as to remove unpleasant odors, dust, bacteria, etc. from the air in the bathroom. The filter 60 may be composed of an antibacterial filter including a photocatalytic coating layer, which is activated by the light generated by the lighting device 15.

The intake vane 22 may include, on the rear surface thereof, a reflector 23 for reflecting the light, generated by the lighting device 15, toward the filter 60. The reflector 23 may be a mirror. The photocatalyst in the filter 60 may be activated by the light generated by the lighting device 15 and reflected by the reflector 23.

For regeneration of the filter 60 for repeated use thereof, the surface of the filter 60 may be coated with a photocatalyst. The coated photocatalyst may be activated by an external light source (a lighting fixture in the bathroom) or the lighting device 15 in the bathroom management apparatus 100. Therefore, since odor particles collected in the filter 60 may decompose into odorless materials, the filter 60 may be regenerated in proportion to the decomposed amount, and thus, the filter may maintain its deodorizing capability upon subsequent repeated operation.

The lower part 14f of the front surface of the inner case 14 may be provided with a discharge grille 18. The discharge grille 18 is provided in the first air discharge port 14b so as to allow the air in the duct 30 to be discharged into the bathroom through the first air discharge port 14b.

The intake vane 22 may be provided at the front face of the combined case 12 and 14 so as to open and close the air intake port 14a. The first discharge vane 24 may be provided at the front face of the combined case 12 and 14 so as to open and close the first air intake port 14b, and the second discharge vane 26 may be provided at the duct 30 so as to open and close the second air discharge port 12a.

The intake vane 22 may be rotatably coupled at the lower end thereof to the intermediate part 14e of the inner case 14. Therefore, as the intake vane 22 is rotated about the lower end thereof serving as the rotational center, the upper end of the intake vane 22 may be separated from the inner case 14, thereby opening the air intake port 14a. Meanwhile, when the upper end of the intake vane 22 is moved toward the inner case 14, the air intake port 14a may be closed.

The first discharge vane 24 may be provided under the intake vane 22. The upper end of the first discharge vane 24 may be provided close to the lower end of the intake vane 22. The first discharge vane 24 is rotatably coupled at the upper end thereof to the intermediate part 14e of the inner case 14 such that the first discharge vane 24 may be rotated about the upper end thereof, which serves as the rotational center. Therefore, as the lower end of the first discharge vane 24 is separated from the inner case 14, the first air discharge port 14b may be opened. Meanwhile, as the lower end of the first discharge vane 24 is moved toward the inner case 14, the first air discharge port 14b may be closed.

The intake vane 22 and the first discharge vane 24 may be rotated to a predetermined angle of approximately 35 degrees with respect to the inner case 14 so as to open the air intake port 14a and the first air intake port 14b, respectively. When the intake vane 22 and the first discharge vane 24 are rotated so as to open the air intake port 14a and the first air discharge port 14b, the air in the bathroom may be introduced into the duct 30 through the upper space defined between the intake vane 22 and the inner case 24 and then into the air intake port 14a. Subsequently, the air introduced into the duct 30 may be discharged into the bathroom through the first air discharge port 14b and then through the lower space defined between the first discharge vane 24 and the inner case 14. In this regard, since a ventilation window may be positioned at an upper level of the bathroom, directing hot air discharged into the bathroom from the duct 30 downward may be advantageous, in terms of circulation of the hot air in the bathroom and the efficiency with which the floor of the bathroom is dried. During the operation of the bathroom management apparatus 100, at least one of the intake vane 22 or the first discharge vane 24 may be rotated so as to control the flowing direction of air. When the bathroom management apparatus 100 is not operated, the intake vane 22 and the first discharge vane 24 may be closed, and the bathroom management apparatus 100 thus becomes more compact in the anteroposterior direction, thereby helping to prevent a user from colliding with the apparatus.

The duct 30 may be coupled to an approximate center of the inner case 14 when viewed in the longitudinal direction. Consequently, one longitudinal end of the inner case 14 may project from the duct 30 in one direction, and the other longitudinal end of the inner case 14 may project from the duct 30 in the opposite direction. Accordingly, when the inner case 14 is fitted into and coupled to the outer case 12, the combined case 12 and 14 may be provided therein with a first electric component compartment S1, defined at one side of the duct 30, and a second electric component compartment S2, defined at the other side of the duct 30.

The first electric component compartment S1 and the second electric component compartment S2 may accommodate electric components that require electricity. In other words, the electric components may be accommodated in the first electric component compartment S1 and the second electric component compartment S2. Consequently, when moisture is introduced into the combined case 12 and 14, it is possible to minimize damage to and malfunction of the electric components due to the moisture since the first and second electrical components are at the sides of the duct 30. The electric components may include an intake vane motor 200, a first discharge vane motor 400, a fan motor 600, a motor 700 and a controller 90. Among these, the intake vane motor 200 and the controller 90 may be accommodated in the first electric component compartment S1, and the first discharge vane motor 400, the fan motor 600, and the motor 700 may be accommodated in the second electric component compartment S2.

A driving motor 200 may be coupled to the rear surface of the inner case 14. The driving motor 200 may be composed of at least one motor so as to concurrently drive (i.e. move) the intake vane 22 and the first discharge vane 24. The driving motor 200 may include an intake vane motor 200, which is provided in the first electric component compartment S1 when coupled to the rear surface of the inner case 14 so as to drive the intake vane 22, and a first discharge vane motor 400, which is provided in the second electric component compartment S2 when coupled to the rear surface of the inner case 14 so as to drive the first discharge vane 24.

The intake vane motor 200 may be coupled to the upper part 14d of the rear surface of the inner case 14, which is spaced apart from the region of the duct 30, and the first discharge vane motor 400 may be coupled to the lower part 14f of the inner case 14, which is spaced apart from another region of the duct 30. The rotating shaft of the intake vane motor 200 may pass through and, thus, may project forward from the inner case 14. A first cam 202 may be coupled to the rotating shaft of the intake vane motor 200, which projects forward from the inner case 14. The first cam 202 may be provided at the front surface of the inner case 14. The rotating shaft of the first discharge vane motor 400 may also pass through the inner case 14 to project forward from the inner case 14. A third cam 402 may be coupled to the rotating shaft of the first discharge vane motor 400, which projects forward from the inner case 14. The third cam 402 may also be provided at the front surface of the inner case 14.

The duct 30 may be provided in the combined case 12 and 14. The duct 30 may be provided in the internal space defined between the rear surface of the inner case 14 and the outer case 12. The duct 30 may serve to connect the air intake port 14a, the first air discharge port 14b and the second air discharge port 12a to each other.

The duct 30 may include an upper front portion and a lower front portion, which are spaced apart from each other and are in an open state. The upper front portion and the lower front portion of the duct 30 may project forward so as to define a recessed space 34 between the upper front portion and the lower front portion. The recessed space 34 defined in the duct 30 may be provided behind the intermediate part 14e so as to correspond to the form of the intermediate part 14e, which is depressed rearward from the inner case 14. The duct 30 may be coupled to the rear surface of the inner case 14 such that the open upper front portion of the duct 30 corresponds to the air intake port 14a and the open lower front portion of the duct 30 corresponds to the first air discharge port 14b. The open lower portion of the duct 30 may be coupled to the lower surface of the outer case 12 so as to correspond to the second air intake port 12a.

The duct 30 may include a main flow channel 31 communicating with the air intake port 14a, a first sub flow channel 32 branched from the main flow channel 31 so as to communicate with the first air discharge port 14b, and a second sub flow channel 33 branched from the main flow channel 31 so as to communicate with the second air discharge port 12a. The main flow channel 31 may be positioned above the first sub flow channel 32 and the second sub flow channel 33. The main flow channel 31 may be coupled to the rear surface of the upper part 14d of the inner case 14 such that the upper end of the main flow channel 31 may correspond to the air intake port 14a. The first sub flow channel 32 may be branched from the lower end of the main flow channel 31, and may be coupled to the rear surface of the lower part 14f of the inner case 14 so as to correspond to the first air discharge port 14b. The second sub flow channel 33 may be branched from the lower end of the main flow channel 31, and may be coupled to the lower surface of the outer case 12 so as to correspond to the second air discharge port 12a.

The blower fan 40 may be provided in the main flow channel 31. The blower fan 40 may extend in a lateral direction, and a longitudinal direction of the blower fan 40 may coincide with the rotational axis of the blower fan 40.

Specifically, the blower fan 40 may be a cross-flow fan configured to suck and discharge air in a radial direction. The main flow channel 31 may include, at left and right ends of an upper portion thereof, fan-mounting holes 36, in which the left and right ends of the blower fan 40 may be fitted. The fan motor 600 for driving the blower fan 40 may be mounted on a lateral surface of the duct 30.

The fan motor 600 may be mounted on the lateral surface of the duct 30 via a fan-motor-mounting bracket 650, and may be provided in the second electric component compartment S2. Specifically, the fan motor 600 may be coupled to a side of the fan-motor-mounting bracket 650, and the fan-motor-mounting bracket 650 may be coupled to the duct 30 while covering the fan-mounting hole 36, with the result that the fan motor 600 may be mounted on the lateral surface of the duct 30. The fan-motor-mounting bracket 650 may be provided with a third through hole 655 through which the rotating shaft 45 of the blower fan 40 may penetrate. The rotating shaft 45 of the blower fan 40 may project from the lateral surface of the duct 30 through the third through hole 655, and may be coupled to the rotating shaft of the fan motor 600. The fan-motor-mounting bracket 650 may be provided with a fifth sealing member 805 for sealing the third through hole 655.

The blower fan 40 may be provided in an upper space of the main flow channel 31 behind the air intake port 14a. The blower fan 40 may suck air through the air intake port 14a and discharge the air through the first air discharge port 14b and the second air discharge port 12a.

The main flow channel 31 may further include the heater 50. The heater 50 may be an electric heater for generating heat using electric power. The heater 50 may extend in a lateral direction. In the main flow channel 31, the blower fan 40 may be provided above the heater 50, and the heater 50 may be provided under the blower fan 40. If the blower fan 40 is provided under the heater 50, the blower fan 40 may suck hot air heated while passing through the heater 50, and deformation due to the hot air may result. Accordingly, it may be preferable that the blower fan 40 be provided above the heater 50 and that the heater 50 be provided under the blower fan 40. The duct 30 may include, in a lateral surface thereof, a heater-mounting hole 38a. The heater-mounting hole 38a may be provided at the lateral surface of the duct 30 under the fan-mounting hole 36. The lateral surface of the duct 30 may include a sixth sealing member 806 that seals the heater-mounting hole 38a.

The duct 30 may further include a flow-channel-changing damper 35. The flow-channel-changing damper 35 may be rotatably provided under a plurality of ionizers 70. The flow-channel-changing damper 35 may enable the main flow channel 31 to selectively communicate with one of the first sub flow channel 32 or the second sub flow channel 33 such that the air, which is introduced into the duct 30 through the air intake port 14a, may flow toward one of the first air discharge port 14b or the second air discharge port 12a.

The flow-channel-changing damper 35 may allow the main flow channel 31 to communicate with the first sub flow channel 32 when the first discharge vane 24 opens the first air discharge port 14b, and may allow the main flow channel 31 to communicate with the second sub flow channel 33 when the second discharge vane 26 opens the second air discharge port 12a. When the main flow channel 31 communicates with the first sub flow channel 32 by the flow-channel-changing damper 35, the air in the duct 30 may be discharged into the bathroom through the first air discharged port 14b. Meanwhile, when the main flow channel 31 communicates with the second sub flow channel 33 by the flow-channel-changing damper 35, the air in the duct 30 is discharged into the bathroom through the second air discharge port 12a.

The duct 30 may include, in the lateral surface thereof, a fourth through hole 38b into which the rotating shaft of the flow-channel-changing damper 35 may be fitted, and a fifth through hole 38c, into which the rotating shaft of the second discharge vane 26 is fitted. The duct 30 may include a seventh sealing member 807 that seals the fourth through hole 38b and an eighth sealing member 808 that seals the fifth through hole 38c.

The motor 700, which is adapted to simultaneously operate the second discharge vane 26 and the flow-channel-changing damper 35, may be coupled to a lateral surface of the duct 30. The motor 700, which may be coupled to the lateral surface of the duct 30 through a first gear module 750, and may be provided in the second electric component compartment S2. In other words, the motor 700 may be coupled to a side surface of the first gear module 750, and the first gear module 750 may be coupled to the lateral surface of the duct 30 so as to cover the fourth through hole 38b and the fifth through hole 38c.

Figure 13:
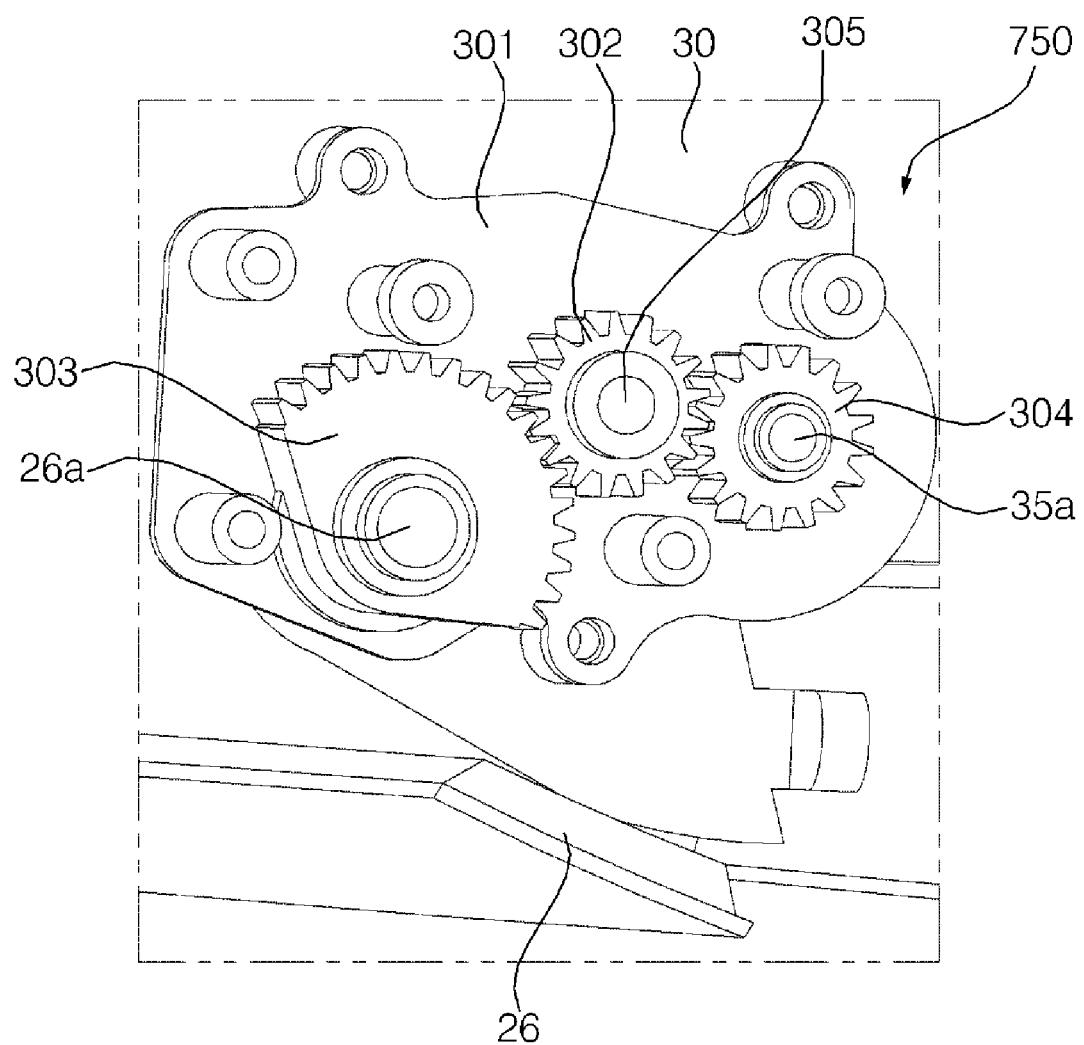
FIG. 13 is a view illustrating the interior structure of the first gear module installed at a lateral side of the duct.

The first gear module 750 may include a plurality of gears that connect the rotating shaft of the motor 700, the rotating shaft of the second discharge vane 26, and the rotating shaft of the flow-channel-changing damper 35 to each other. Accordingly, the first gear module 750 may serve to simultaneously transmit the rotative force from the rotating shaft of the motor 700 to both the rotating shaft of the first discharge vane 24 and the rotating shaft of the flow-channel-changing damper 35 so as to simultaneously rotate the first discharge vane 24 and the flow-channel-changing damper 35 using the rotative force of the motor 700. The first gear module 750 will be described in detail later with reference to FIG. 13.

The plurality of ionizers 70 may be provided on the rear surface of the duct 30 in the main flow channel 31. The plurality of ionizers 70 may generate a large amount of cations and anions (hereinafter, referred to as ions) into the duct 30. Consequently, the air, which is discharged through the first air discharge port 14b and the second air discharge port 12a, may contain the ions generated from the plurality of ionizers 70. The ions, which are discharged into the bathroom, react with microorganisms and bacteria in the bathroom, thereby breaking down DNA and thus causing necrosis of the microorganisms and the bacteria. Furthermore, the ions react with fungi or mold, thereby suppressing the growth of fungi and mold. The rear surface of the duct 30 that is defined in the main flow channel 31 may include ionizer-mounting holes 37 into which respective ones among the plurality of ionizers 70 may be fitted. The ionizer-mounting holes 37 may communicate with the internal space of the duct 30. The plurality of ionizers 70 may be laterally spaced apart from each other. The ionizer-mounting holes 37 may include a number of ionizer-mounting holes corresponding to the number of the plurality of ionizers 70. The duct 30 may be provided with ninth sealing members 809 that seal the ionizer-mounting holes 37.

The plurality of ionizers 70 may be provided under the heater 50 but above the first sub flow channel 32 and the second sub flow channel 33, and relatively close to the first sub flow channel 32 and the second sub flow channel 33. Specifically, since the ion particles generated from the plurality of ionizers 70 can survive for a long period of time when there is no collision with a structure, it may be preferable that the plurality of ionizers 70 are provided under the heater 50 and close to the first sub flow channel 32 and the second sub flow channel 33. Consequently, the air, which is introduced into the main flow channel 31 through the air intake port 14a by means of the suction power of the blower fan 40, may flow to the heater 50 due to the blower fan 40, and is heated by the heater 50, resulting in hot air. The hot air is provided with ions generated from the plurality of ionizers 70, and is discharged into the bathroom through one of the first air discharge port 14b and the second air discharge port 12a.

The combined case 12 and 14 may be provided at the lower surface thereof with a hanger 80. The hanger 80 may be coupled to the lower surface of the outer case 12 so as to substantially correspond to the second air discharge port 12a. The hanger 80 may be coupled to the lower surface of the outer case 12 so as to project outward from the outer case 12.

A towel 1 may be hung on the region of the hanger that corresponds to the second air discharge port 12a. A user may remove moisture remaining on his/her body using a towel 1 after face-washing, hand-washing, showering, etc., and hangs the towel containing moisture on the hanger 80. The wet towel 1 hanging on the hanger 80 may be dried and sterilized by the air discharged through the second air discharge port 12a. The second air discharge port 12a may be preferably configured to discharge air toward the hanger 80 so as to dry and sterilize the towel 1 hanging on the hanger 80. In other words, the air discharged through the first air discharge port 14b may function to dry and sterilize the inside of the bathroom, and the air discharged through the second air discharge port 12a may function to dry and sterilize the towel 1.

Microorganisms and bacteria may also be present on a wet towel 1, furniture, etc. Hence, unpleasant odors may be generated from the wet towel 1, and the contaminated towel 1 or the like may serve as a medium capable of transmitting contaminations to others. The towel 1 may be repeatedly used for one day to two days for face-washing or other activities in the bathroom. Since the bathroom is a damp space, moisture remaining in the towel 1 may serve as an optimal site for the growth of bacteria that use dermal tissue, separated from human skin, as nutrition.

The bathroom management apparatus 100 may be able to sterilize the wet towel 1, sterilize furniture or other objects using ions generated from the ionizers 70, and may be able to improve the antiseptic effect to 99% when using hot air generated from the heater 50. This antiseptic effect is achieved through a mechanism for completely evaporating even a slight amount of moisture remaining in the towel 1 by increasing the difference in the water-vapor partial pressure of the high-temperature and low-humidity air. The bathroom management apparatus 100 may be designed so as to reduce energy consumption by restricting the operation of the heater 50 at the end of sterilization process.

The left portion or right portion of the outer case 12 may be extended leftward or rightward so as to provide a toothbrush compartment for accommodating toothbrushes therein while a flow channel is further branched from the main flow channel 31 under the ionizers 70 and is connected to the toothbrush compartment. This configuration may promptly dry and sterilize toothbrushes contained in the toothbrush compartment by introducing the air containing ions generated from the ionizers 70 into the toothbrush compartment. The ionizers 70 and the heater 50 may be concurrently operated so as to supply hot air containing ions to the toothbrush compartment and to more efficiently dry and sterilize the toothbrushes. A flow channel may be further branched from the main flow channel 31, and a damper for opening and closing the flow channel leading to the toothbrush compartment may be provided. Furthermore, the toothbrush compartment may include a toothbrush hanger to receive toothbrushes. In addition, the toothbrush compartment may include an ultraviolet light-emitting diode that sterilizes toothbrushes.

The bathroom management apparatus 100 according to the embodiment of the present disclosure may further include the controller 90. The controller 90, which may control the operation of the bathroom management apparatus 100, may be coupled to the rear surface of the inner case 14 and may be provided in the first electric component compartment S1 to be spaced apart from a lateral side of the duct 30.

Referring to FIGS. 8 to 13, the first gear module 750 may include a first gear box 301 defining the appearance of the module. The first gear box 301 may be coupled to a lateral side of the duct 30. A first drive gear 302, a first driven gear 303 and a second driven gear 304 may be rotatably provided in the first gear box 301. The first drive gear 302 may be provided between the first driven gear 303 and the second driven gear 304 when being engaged therewith. Specifically, the first driven gear 303 may be provided at a side of the first drive gear 302 while being engaged therewith, and the second driven gear 304 may be provided at an opposite side of the drive gear 302 while being engaged therewith.

The rotating shaft 305 of the motor 700 may penetrate the first gear box 301 and may be coupled to the first drive gear 302. The first driven gear 303 may be coupled to the rotating shaft 26a of the second discharge vane 26, and the second driven gear 304 may be coupled to the rotating shaft 35a of the flow-channel-changing damper 35. Accordingly, when the motor 700 is activated, the first drive gear 302 may be rotated together with the rotating shaft 305 by the driving force of the motor 700, and at the same time, the first driven gear 303 and the second driven gear 304 may be rotated to concurrently rotate the second discharge vane 26 and the flow-channel-changing damper 35.

In this configuration, when the second discharge vane 26 closes the second air discharge port 12a, the flow-channel-changing damper 35 may cause the main flow channel 31 to communicate with the first sub flow channel 32 while blocking the communication between the main flow channel 31 and the second sub flow channel 33. In this state, when the second discharge vane 26 is rotated so as to open the second air discharge port 12a, the flow-channel-changing damper 35 may be rotated together with the second discharge vane 26 so as to cause the main flow channel 31 to communicate with the second sub flow channel 33 while blocking the communication between the main flow channel 31 and the first sub flow channel 32. In one example, the first driven gear 303 and the second driven gear 304 may be configured to have a gear ratio of 2:1.

As described above, the bathroom management apparatus 100 according to the embodiment of the present disclosure may concurrently operate the second discharge vane 26 and the flow-channel-changing damper 35 using the single motor 700. The second discharge vane 26 may open the second air discharge port 12a, and the flow-channel-changing damper 35 may allow the main flow channel 31 to communicate with the second sub flow channel 33 only when the bathroom management apparatus 100 is operated in a mode of sterilizing and drying an object, such as a wet towel 1 hanging on the hanger 80. At this time, the first discharge vane 24 may close the first air discharge port 14b, and the flow-channel-changing damper 35 may block the air flow between the main flow channel 31 and the first sub flow channel 32.

When the bathroom management apparatus 100 is operated in a mode other than the mode of sterilizing and drying a wet towel 1 hanging on the hanger 80 or other objects, the first discharge vane 24 may open the first air discharge port 14b, and the flow-channel-changing damper 35 may allow the air flow between the main flow channel 31 and the first sub flow channel 32. At this time, the second discharge vane 26 may close the second air discharge port 12a, and the flow-channel-changing damper 35 may block the air flow between the main flow channel 31 and the second sub flow channel 33.

Referring to FIGS. 7 and 14 to 19, the intake vane 22 may include, on the rear surface thereof, a second cam 203, which is moved by the first cam 202 so as to open the intake vane 22. The first discharge vane 24 may include, on the rear surface thereof, a fourth cam 403, which is moved by a third cam 402 so as to open the first discharge vane 24.

The rotating shaft 201 of the intake vane motor 200 may pass through the inner case 14 and project forward from the inner case 14. The first cam 202 may be coupled to the rotating shaft 201 of the intake vane motor 200. The first cam 202 may be coupled to the portion of the rotating shaft 201 that projects forward from the inner case 14 through the inner case 14, and may be provided in front of the inner case 14. The first cam 202 may include, on the front surface thereof, a first inclined portion 202a. The intake vane 22 may include, on the lower end of the rear surface thereof, the second cam 203, which projects rearward. The second cam 203 may include, on the rear surface thereof, a second inclined portion 203a corresponding to the first inclined portion 202a.

Due to the presence of the first inclined portion 202a and the second inclined portion 203a, as the first cam 202 is rotated together with the rotating shaft 201 of the intake vane motor 200 by the driving force of the intake vane motor 200, the first cam 202 may push the second cam 203 forward, thereby opening the intake vane 22. As the intake vane motor 200 is rotated so as to allow the intake vane 22 to be closed from the opened state, the intake vane 22 may be closed by the restoring force of a first return spring 210.

The rotating shaft 401 of the first discharge vane motor 400 may pass through an opening in the inner case 14 and may project rearward from the inner case 14. The third cam 402 may be coupled to the rotating shaft 401 of the first discharge vane motor 400. The third cam 402 may be coupled to the portion of the rotating shaft 401 that passes through the inner case 14 and projects forward from the inner case 14, and may be provided in front of the inner case 14. The third cam 402 may include, on the front surface thereof, a third inclined portion 402a. The first discharge vane 24 may include, on the upper end of the rear surface thereof, the fourth cam 403, which projects rearward. The fourth cam 403 may include, on the rear surface thereof, a fourth inclined portion 403a corresponding to the third inclined portion 402a.

Due to the presence of the third inclined portion 402a and the fourth inclined portion 403a, as the third cam 402 is rotated together with the rotating shaft 401 by the driving force of the first discharge vane motor 400, the third cam 402 may push the fourth cam 403 forward, thereby opening the first discharge vane 24. As the first discharge vane motor 400 is rotated so as to allow the first discharge vane 24 to be closed from the opened state, the first discharge vane 24 may be closed by the restoring force of a second return spring 410.

As described above, since the rear surface of the second cam 203 formed on the intake vane 22 may include the second inclined portion 203a and the front surface of the first cam 202 coupled to the rotating shaft 201 of the intake vane motor 200 may include the first inclined portion 202a, the intake vane 22 can be manually opened by a user. Similarly, since the rear surface of the fourth cam 403 formed on the first discharge vane 24 may include the fourth inclined portion 403a and the front surface of the third cam 402 coupled to the rotating shaft 401 of the first discharge vane motor 400 may include the third inclined portion 402a, the first discharge vane 24 can be manually opened by the user.

In this way, since the intake vane 22 and the first discharge vane 24 can be manually opened by the user, a user can easily access the interior of the bathroom management apparatus 100 to perform replacement of the filter 60 and cleaning of the interior of the duct 30 and the blower fan 40. When a user manually open one of the intake vane 22 or the first discharge vane 24 during the operation of the bathroom management apparatus 100 (i.e. during operation of the blower fan), a hall sensor (not shown) may detect the opening of one of the intake vane 22 or the first discharge vane 24 and transmits a signal indicating the opening to the controller 90, which can stop the operation of the bathroom management apparatus 100.

The intake vane 22 may include, on the rear surface thereof, a first sealing member 801 that seals the gap between the intake vane 22 and the upper part 14d of the inner case 14, and the first discharge vane 24 may include, on the rear surface thereof, a second sealing member 802 that seals the gap between the first discharge vane 24 and the lower part 14f of the inner case 14. The first sealing member 801 may be provided on the upper marginal region and the two side marginal regions of the rear surface of the intake vane 22, and the second sealing member 802 may be provided on the lower marginal region and the two side marginal regions of the rear surface of the first discharge vane 24. The first sealing member 801 and the second sealing member 802 may function to prevent moisture from entering a space between the intake vane 22 and the inner case 14 and a space between the first discharge vane 24 and the inner case 14 when the intake vane 22 and the first discharge vane 24 are in the closed state.

If moisture enters the space between the intake vane 22 and the inner case 14 and between the first discharge vane 24 and the inner case 14 even though the first sealing member 801 is provided on the rear surface of the intake vane 22 and the second sealing member 802 is provided on the rear surface of the first discharge vane 24, it is possible to prevent the entry of the moisture into the duct 30 and the combined case 12 and 14 by promptly discharging the moisture to the outside. This will now be described.

The intake vane 22 may include, on both lateral edges of the rear surface thereof, first hinge portions 25 projecting therefrom, and the first discharge vane 24 may include, on both lateral edges of the rear surface thereof, second hinge portions 27 projecting therefrom. By fitting hinge shafts (not shown) provided at the intermediate part 14e of the inner case 14 into the first hinge portions 25 and the second hinge portions 27, the first hinge portions 25 may couple the lower end of the intake vane 22 to the intermediate part 14e of the inner case 14 in a rotatable manner, and the second hinge portions 27 may couple the upper end of the first discharge vane 24 to the intermediate part 14e of the inner case 14 in a rotatable manner.

The two first hinge portions 25 may be formed on the rear surface of the intake vane 22 so as to have curved surfaces and to project rearward, and may be received in the intermediate part 14e of the inner case 14. Similarly, the two second hinge portions 27 may also be formed on the rear surface of the first discharge vane 24 so as to have curved surfaces and to project rearward, and may be received in the intermediate part 14e of the inner case 14.

The region of the rear surface of the intake vane 22 between the two first hinge portions 25 and the region of the rear surface of the first discharge vane 24 between the two second hinge portions 27 may define a first flow channel 21, which is not included in the intermediate part 14e. Consequently, even when moisture enters the space between the intake vane 22 and the inner case 14, the moisture may flow downward through the first flow channel 21, thereby preventing entry of moisture into the duct 30.

The first flow channel 21 may be positioned at the region defined between the air intake port 14a and the first air discharge port 14b and may be a horizontal length corresponding to the length of the air intake port 14a and the first air discharge port 14b. One end of the first flow channel 21 may correspond to one end of the air intake port 14a and one end of the first air discharge port 14b, and the other end of the first flow channel 21 may correspond to another end of the air intake port 14a and another end of the first air discharge port 14b.

For more efficient water discharge, the first discharge vane 24 may include, in the rear surface thereof, water discharge grooves 28 and 29. The water discharge grooves 28 and 29 may be provided under the first flow channel 21 and extend vertically. The water discharge grooves 28 and 29 may include a first water discharge groove 28, which is positioned so as to correspond to the one end of the first flow channel 21, and a second water discharge groove 29, which is positioned so as to correspond to the other end of the first flow channel 21. Since the first water discharge groove 28 is positioned so as to correspond to the one end of the first flow channel 21 and the second water discharge groove 29 is positioned so as to correspond to the other end of the first flow channel 21, the moisture passed through the first flow channel 21 can be directly discharged downward without laterally spreading outwards.

The second sealing member 802 may not be provided on the region of the rear surface of the first discharge vane 24 that corresponds to the first water discharge groove 28 or on the region of the rear surface of the first discharge vane 24 that corresponds to the second water discharge groove 29. Consequently, the moisture, which has passed through the first water discharge groove 28 and the second water discharge groove 29, can be discharged to the outside from the lower end of the first discharge vane 24 without interferences by the second sealing member 802.

The inner case 14 may include a first through hole 14h through which the rotating shaft 201 of the intake vane motor 200 passes, and a second through hole 14k through which the rotating shaft 401 of the first discharge vane motor 400 passes. Hence, moisture may enter the space between the intake vane 22 and the inner case 14 and the space between the first discharge vane 24 and the inner case 14 through the first through hole 14h and the second through hole 14k. In order to prevent such entry, the first through hole 14h may be provided therein with a third sealing member 803, and the second through hole 14k may be provided therein with a fourth sealing member 804.

Figure 3:
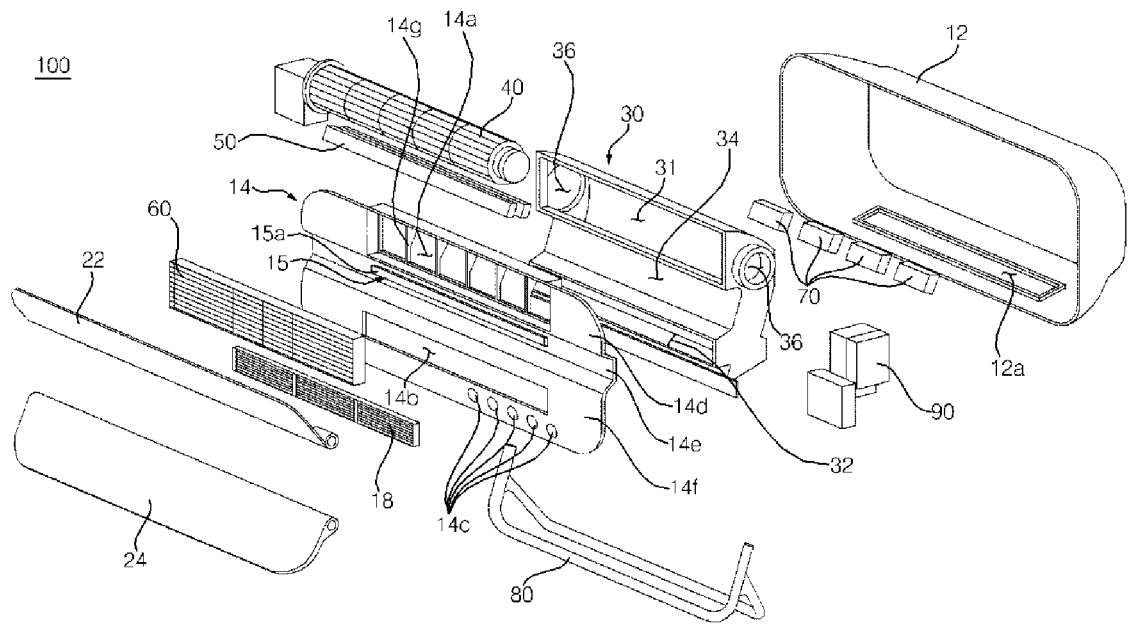
FIG. 3 is an exploded perspective view of FIG. 1.
Figure 4:
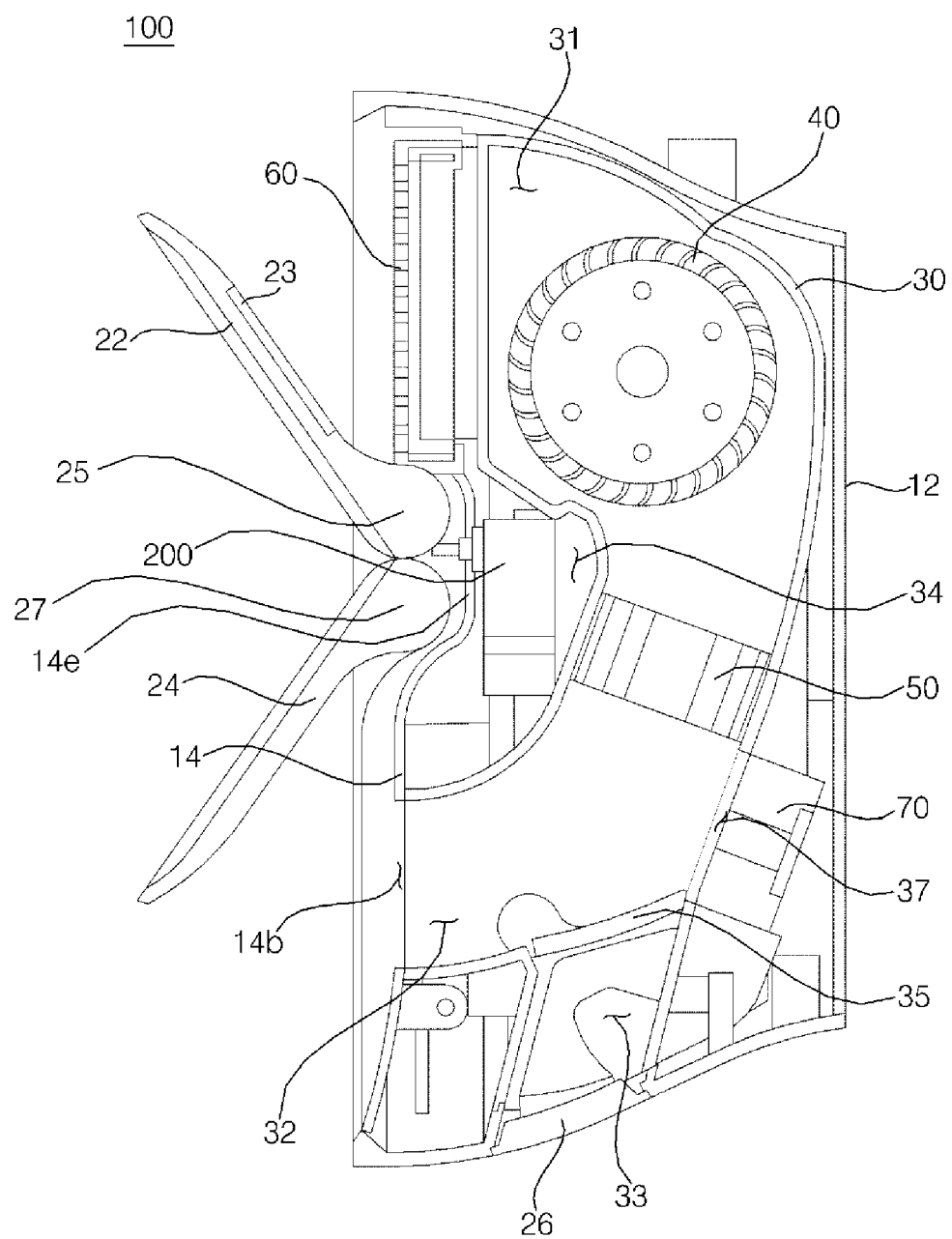
FIG. 4 is a side cross-sectional view of FIG. 2.
Figure 5:
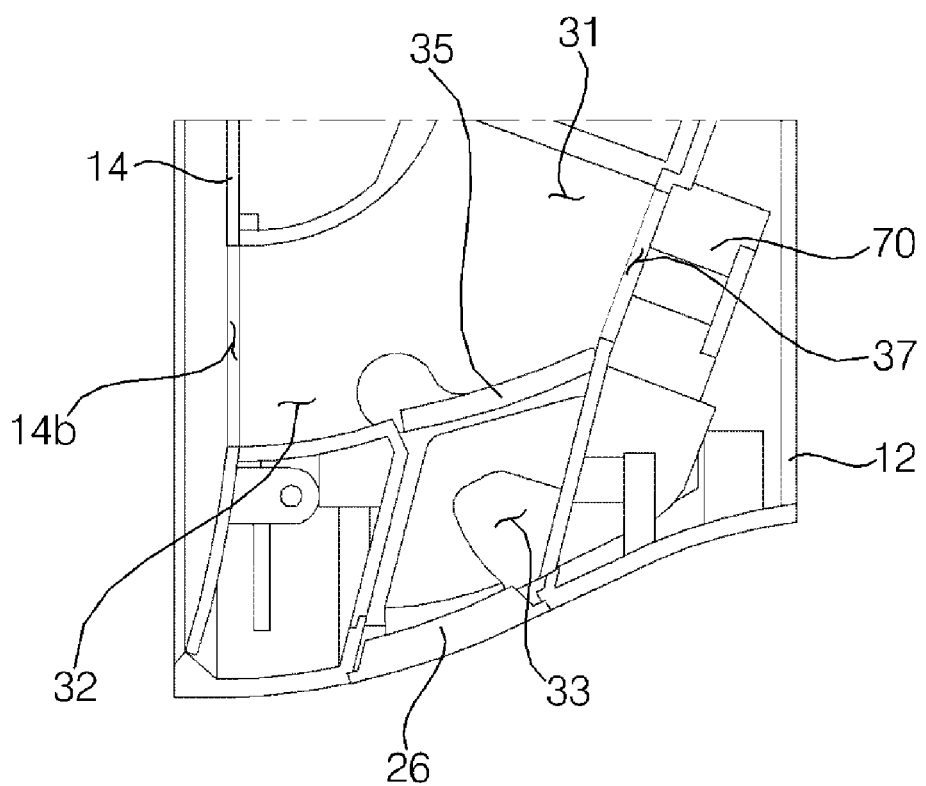
FIG. 5 is a side cross-sectional view illustrating a lower portion of the bathroom management apparatus according to the embodiment of the present disclosure.
Figure 6:
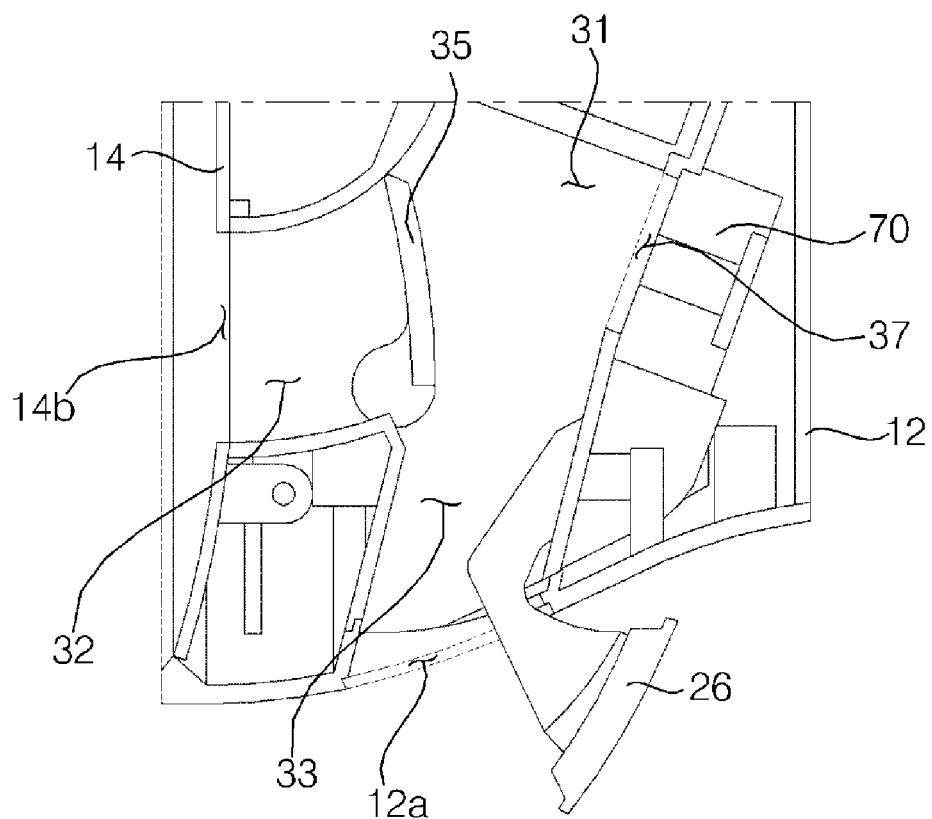
FIG. 6 is a view illustrating a second discharge vane shown in FIG. 5, which is in the open state.
Figure 7:
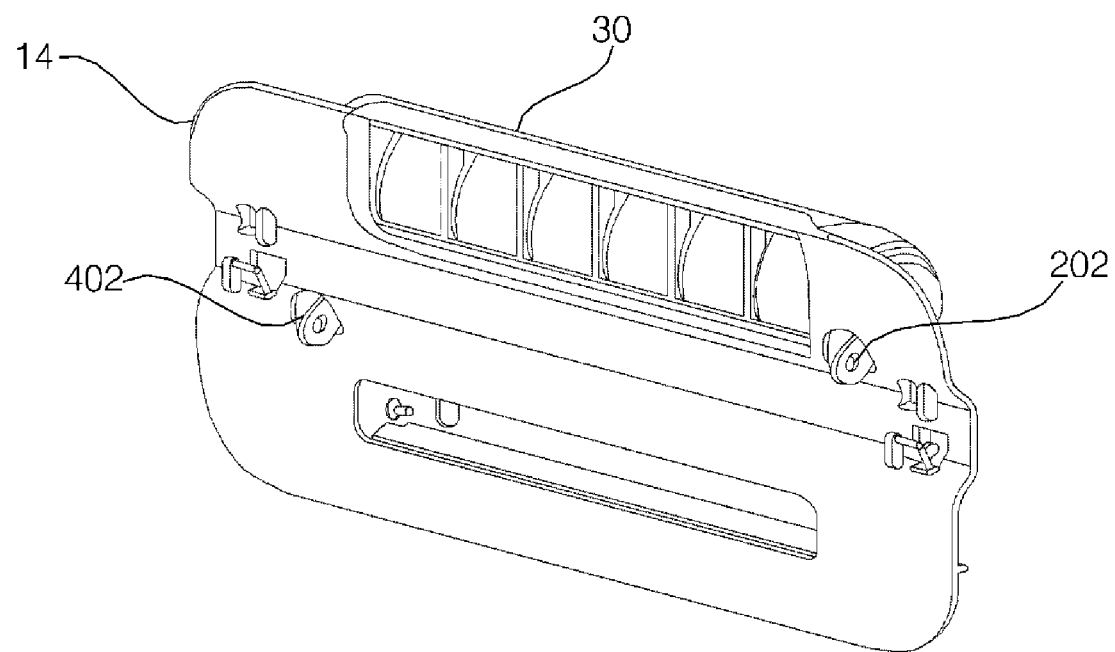
FIG. 7 is a front perspective view illustrating an inner case and a duct of the bathroom management apparatus according to the embodiment of the present disclosure, which are coupled to each other.
Figure 8:
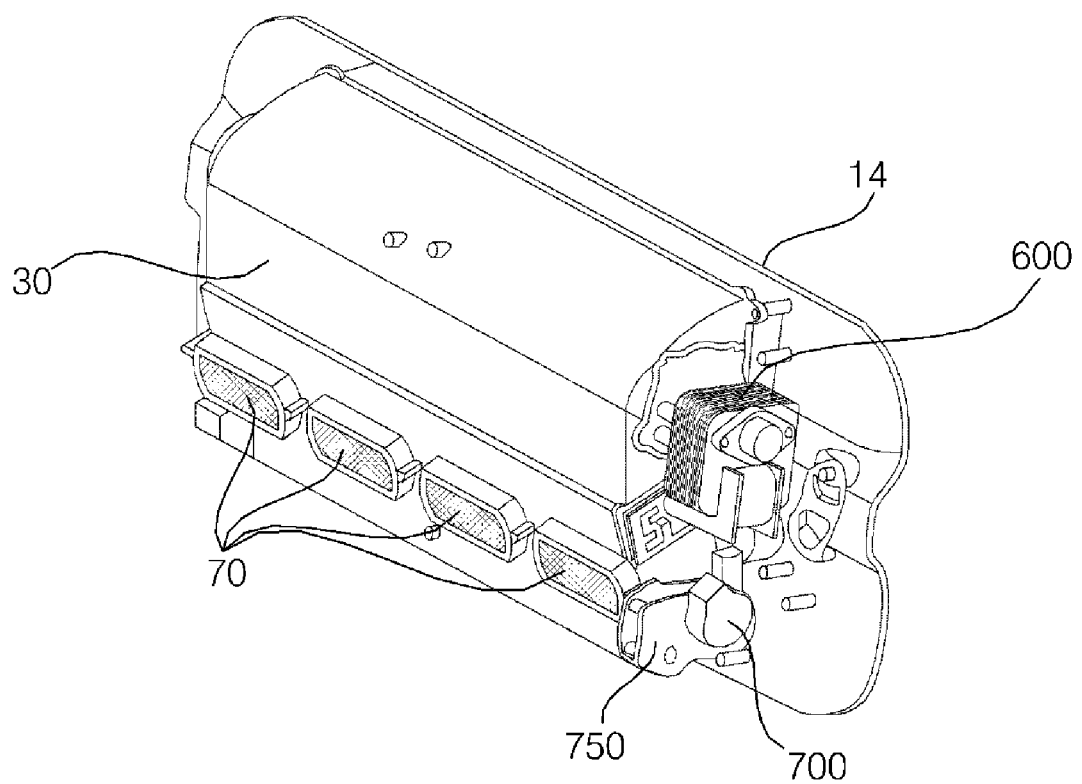
FIG. 8 is a rear perspective view illustrating the inner case and the duct of the bathroom management apparatus according to the embodiment of the present disclosure, which are coupled to each other.
Figure 9:
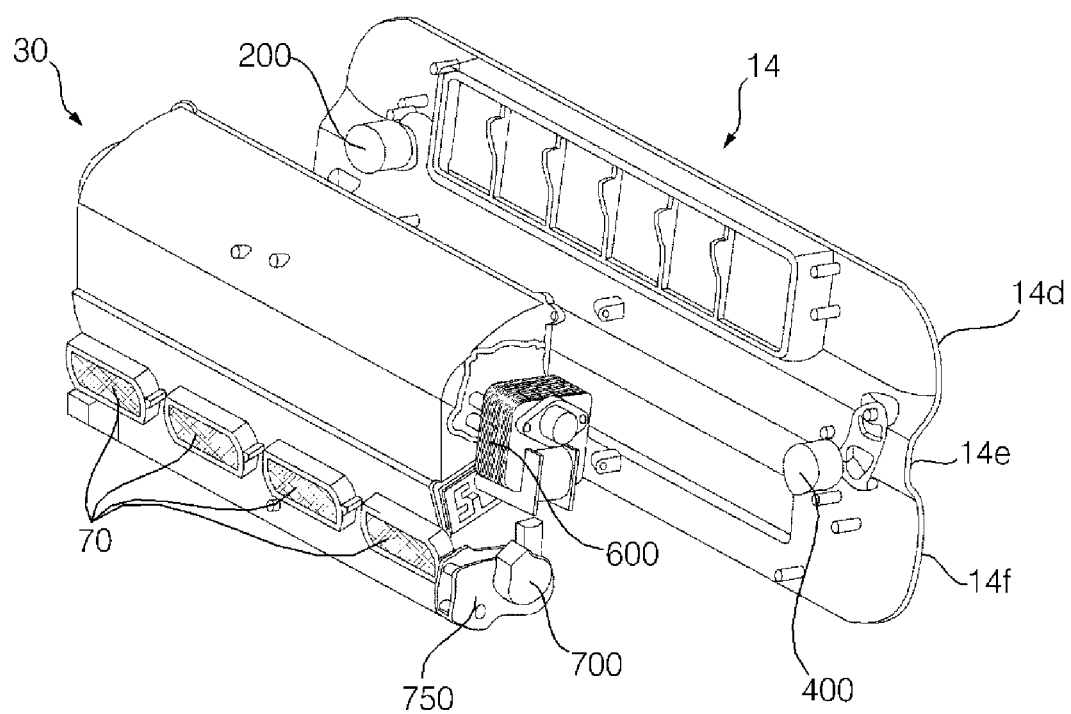
FIG. 9 is a rear perspective view illustrating the inner case and the duct of the bathroom management apparatus according to the embodiment of the present disclosure, which are separated from each other.
Figure 10:
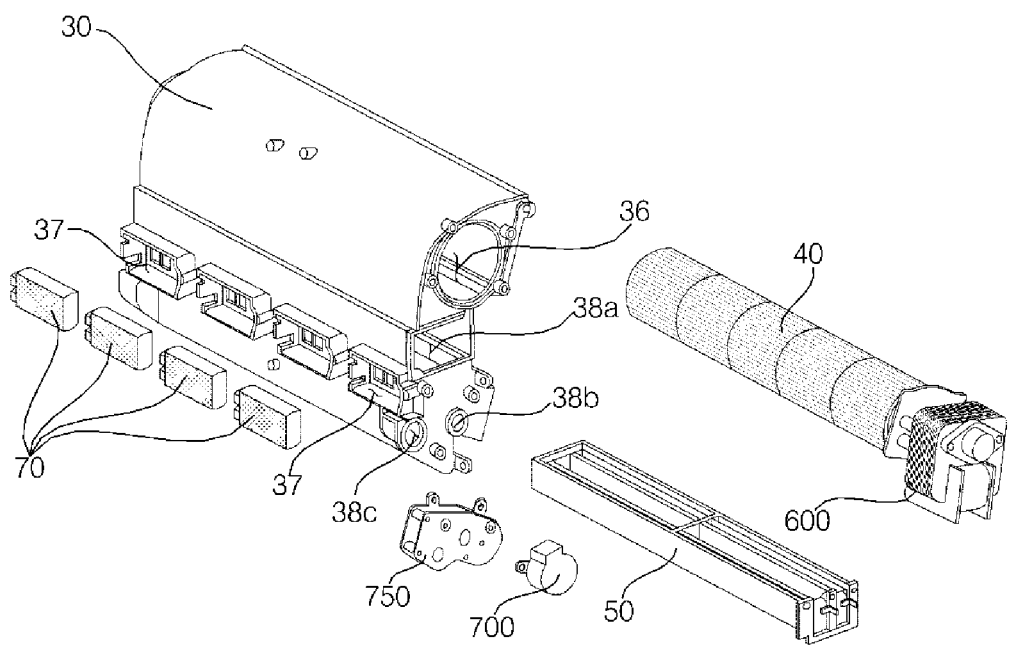
FIG. 10 is an exploded perspective view illustrating a duct module of the bathroom management apparatus according to the embodiment of the present disclosure.
Figure 11:
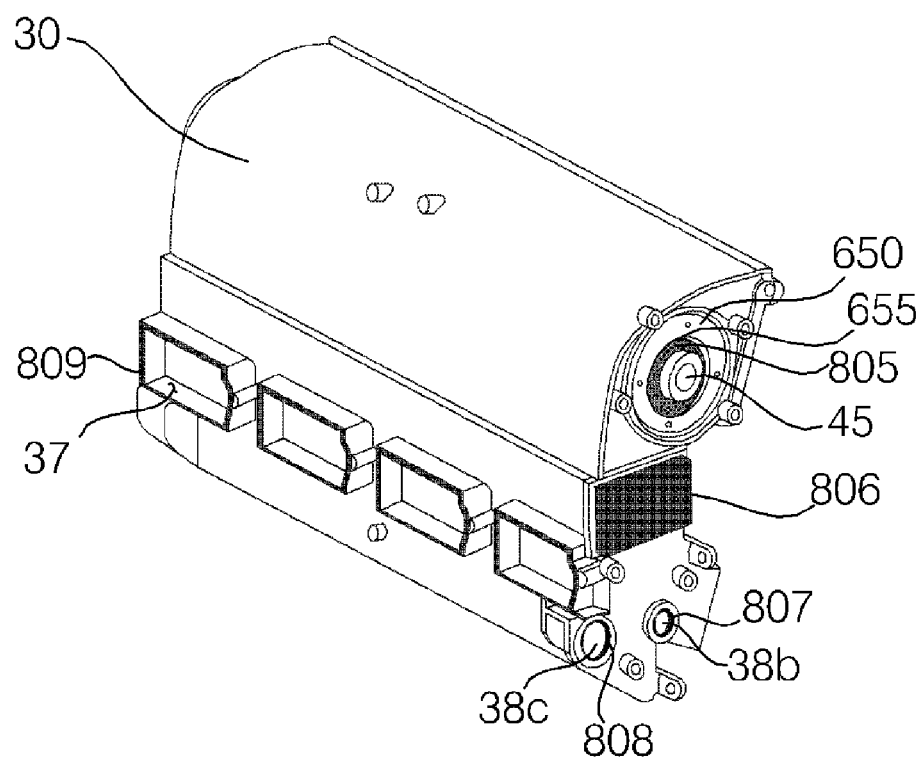
FIG. 11 is a rear perspective view illustrating a blower fan and a heater mounted on the duct of the bathroom management apparatus according to the embodiment of the present disclosure.
Figure 12:
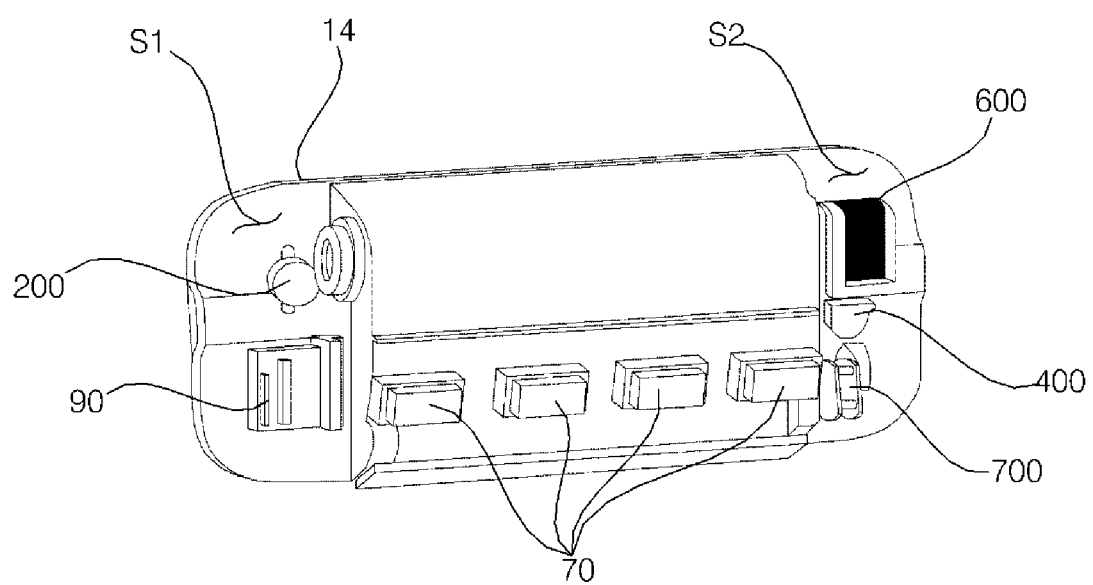
FIG. 12 is a rear perspective view illustrating the duct and electric components mounted on the inner case of the bathroom management apparatus according to the embodiment of the present disclosure.
Figure 20:
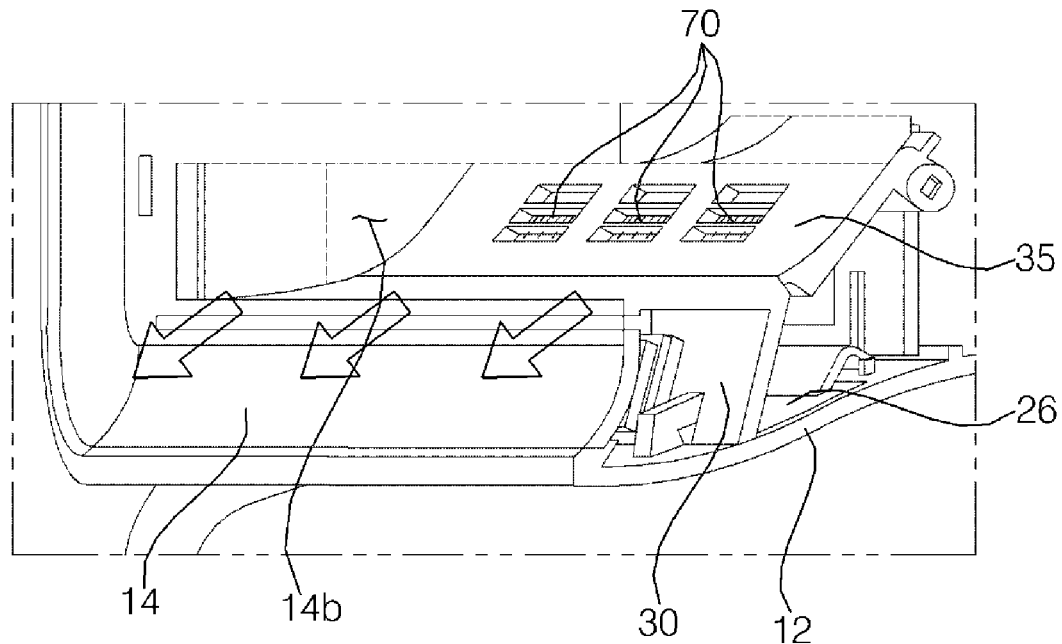
FIGS. 20 and 21 are views illustrating another embodiment of the flow-channel-changing damper.
Figure 21:
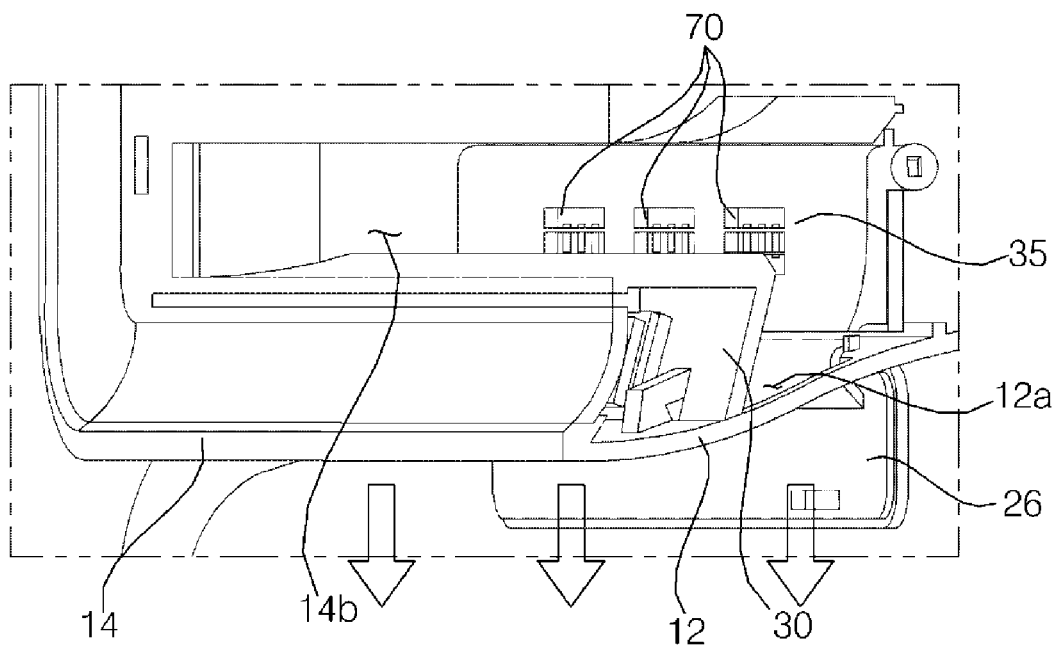

Since the ionizers 70, shown in FIGS. 3 and 4, may be provided relatively close to the first sub flow channel 32 and the second sub flow channel 33, the ionizers 70 are typically not provided in the duct 30 in this embodiment. Another embodiment in which the ionizers 70 are provided in another component will now be described with reference to FIGS. 20 and 21. FIGS. 20 and 21 are views illustrating another embodiment of the flow-channel-changing damper.

Referring to FIGS. 20 and 21, the ionizers 70 may be provided at the flow-channel-changing damper 35. When the flow-channel-changing damper 35 closes the second sub flow channel 33 while the second discharge vane 26 opens the second air discharge port 12a as shown in FIG. 20, the heated air in the main flow channel 31, may receive ions generated from the plurality of ionizers 70 at the inlet of the first sub flow channel 32, and may be discharged into the bathroom through the first air discharge port 14b, thereby drying and sterilizing the floor of the bathroom. When the flow-channel-changing damper 35 closes the second sub flow channel 33 while the second discharge vane 26 opens the second air discharge port 12a as shown in FIG. 21, the heated air in the main flow channel 31, may receive ions generated from the plurality of ionizers 70 at the inlet of the second flow channel 33 and may be discharged into the bathroom through the second air discharge port 12a, thereby drying and sterilizing an object such as wet a towel hanging on the hanger 80.

Figure 22:
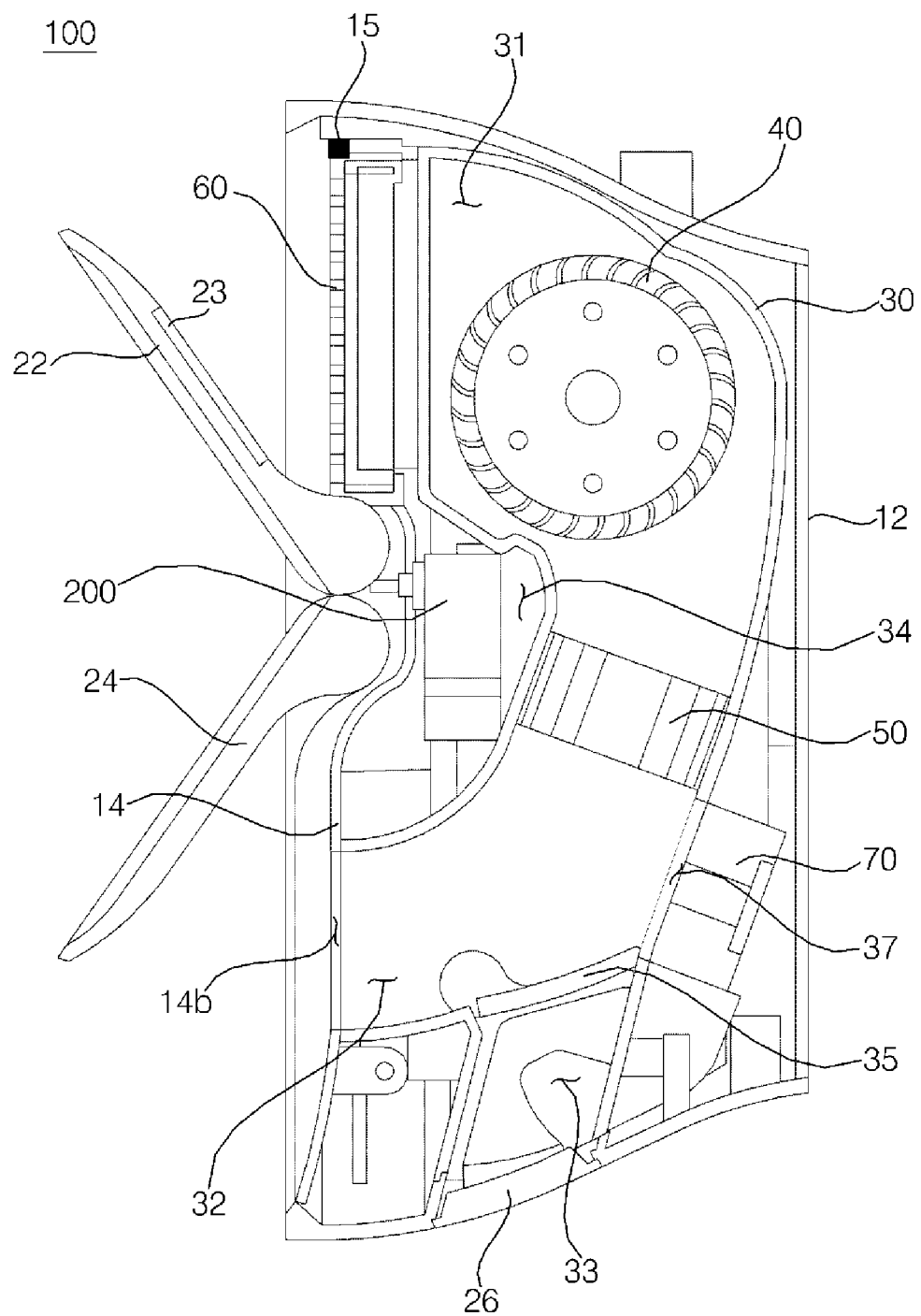
FIGS. 22 to 24 are views of other embodiments in which the position of the lighting device is changed.
Figure 23:
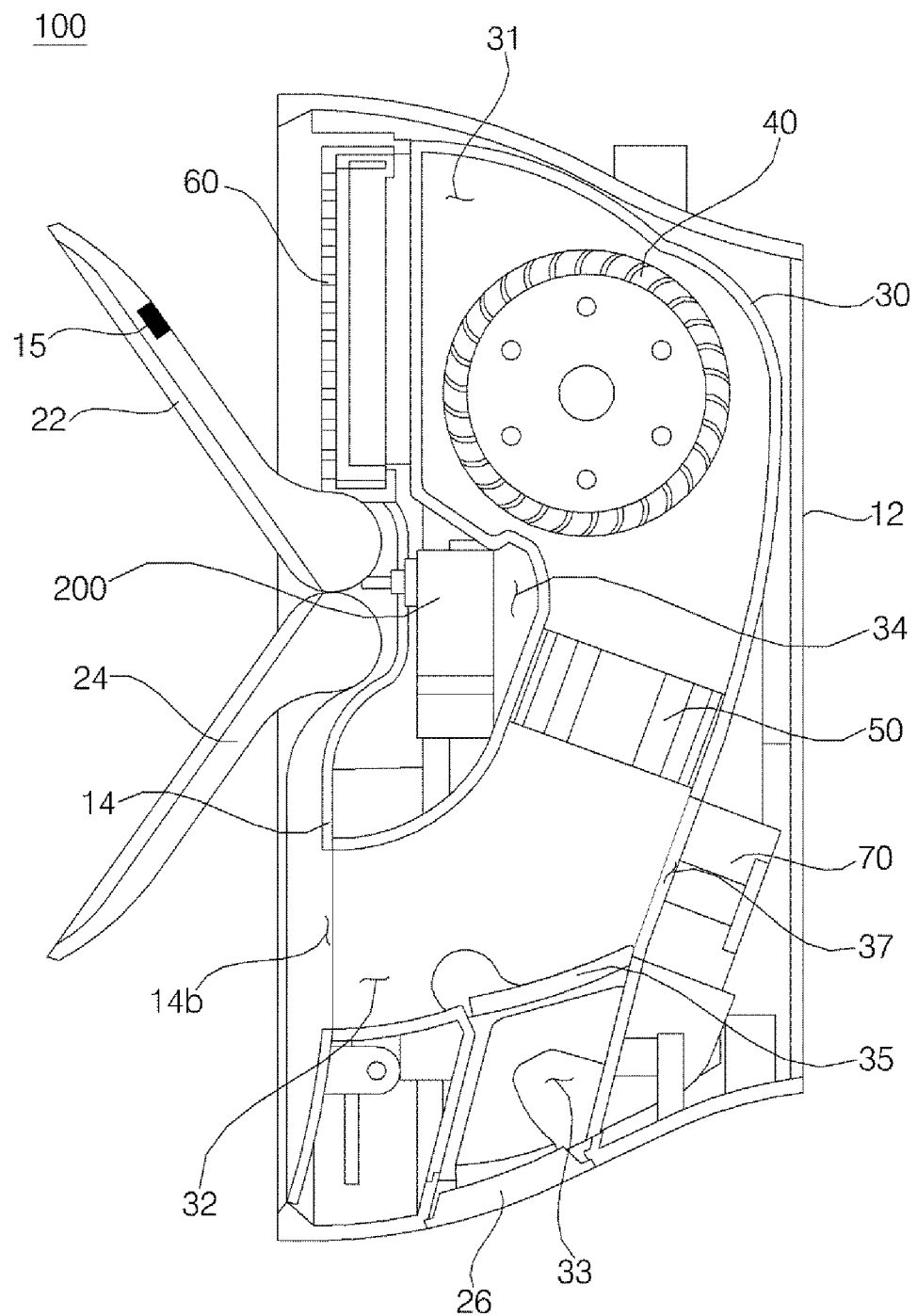
Figure 24:
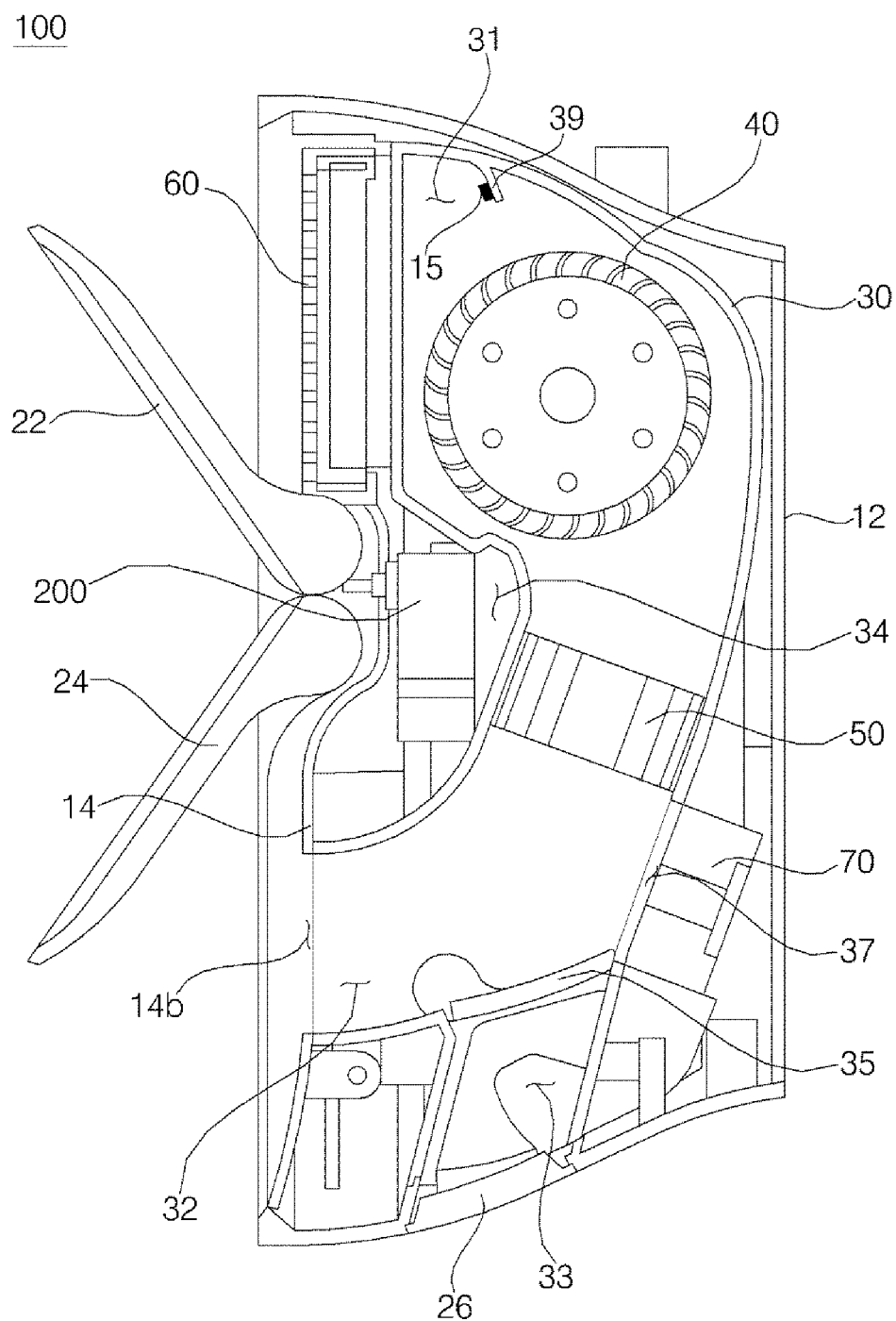

Referring to FIGS. 3 and 4, although the lighting device 15 is installed at the intermediate part 14e of the inner case 14, the position of the lighting device 15 may be variously changed. The reflector 23 may be excluded or may be provided away from the rear surface of the intake vane 22 depending on the position of the lighting device 15. Hereinafter, an embodiment in which the position of the lighting device 15 is changed will be described with reference to FIGS. 22 to 24. FIGS. 22 to 24 are views of other embodiments in which the position of the lighting device is changed.

Referring to FIG. 22, the lighting device 15 may be provided on the upper part 14d of the inner case 14. Specifically, the lighting device 15 may be provided on a region of the inner case 14 above the air intake port 14a. The intake vane 22 may include, on the rear surface thereof, the reflector 23 to reflect light emitted from the lighting device 15 toward the filter 60.

Referring to FIG. 23, the lighting device 15 may be provided on the rear surface of the intake vane 22. The lighting device 15 may generate light and radiate the light directly to the filter 60. Accordingly, the reflector 23 may be omitted from the rear surface of the intake vane 22.

Referring to FIG. 24, the lighting device 15 may be provided in the duct 30. The duct 30 may be provided with an attachment 39, which projects into the main flow channel 31, and the lighting device 15 may be coupled to the attachment 39. The lighting device 15 may generate light and directly radiate the light to the filter 60. Accordingly, the reflector 23 may be omitted from the rear surface of the intake vane 22.

When the lighting device 15 is provided as shown in FIGS. 3, 22 and 23, the lighting device 15 can radiate light to the filter 60 when the intake vane 22 is opened. Meanwhile, when the lighting device 15 is provided in the duct 30 as shown in FIG. 24, it is possible to radiate light to the filter 60 so as to activate a photocatalyst in the filter 60 and to provide an aesthetic benefit of indirect illumination when viewed from the outside when the intake vane 22 is closed. As described above, in the bathroom management apparatus 100 according to certain embodiments of the present disclosure, the lighting device 15 may function to activate the photocatalyst in the filter 60, may be provided at various positions, and may be used as indirect illumination for a bathroom.

Figure 25:
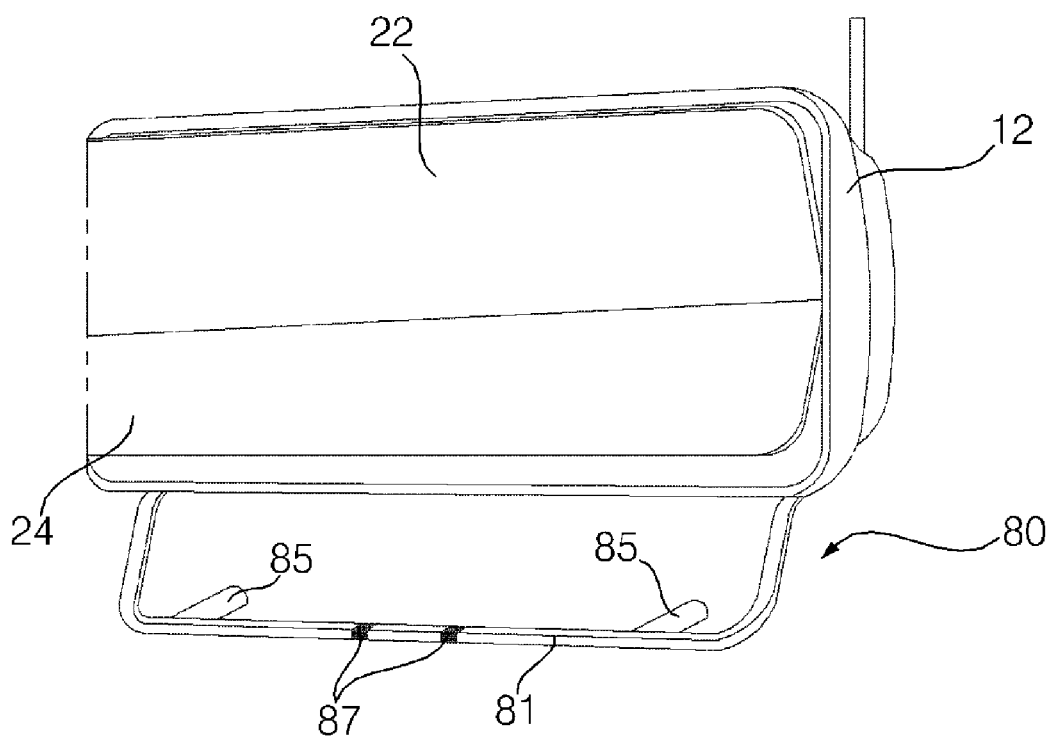
FIG. 25 is a view illustrating a first embodiment of a hanger.
Figure 26:
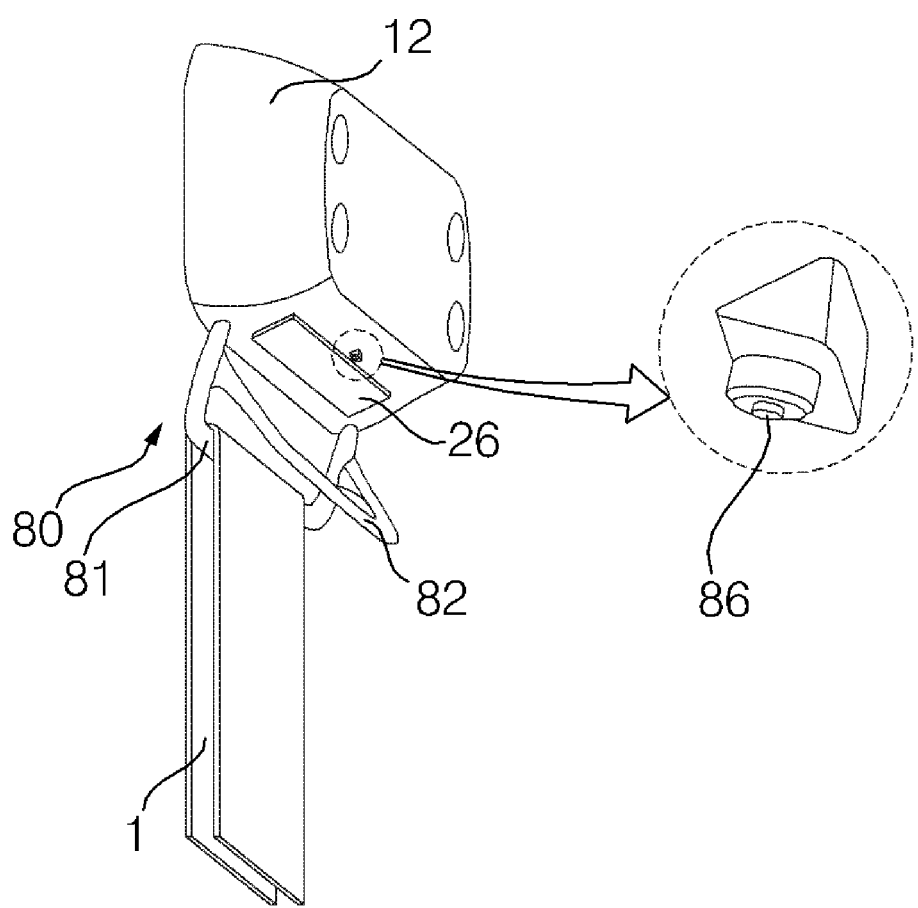
FIG. 26 is a view illustrating a second embodiment of a hanger.

FIG. 25 is a view illustrating a first embodiment of a hanger, and FIG. 26 is a view illustrating a second embodiment of a hanger. Referring to FIGS. 25 and 26, the hanger 80 may include a single hanger part 81 (also referred to as a bar or cylinder) as shown in FIG. 25, or may include two hanger parts (also referred to as bars or cylinders) 81 and 82 as shown in FIG. 26. When the hanger 80 includes a first hanger part 81 and a second hanger part 82, the second hanger part 82 may be spaced apart from the first hanger part 81 rearward, as shown in FIG. 26. In the following disclosure, an embodiment in which the hanger 80 includes the first hanger part 81 and the second hanger part 82 will be described.

Referring to FIG. 26, the hanger 80 may include the first hanger part 81 and the second hanger part 82. The first hanger part 81 may extend horizontally at a lower portion of the hanger 80, and the opposite ends of the first hanger part 81 may be bent upward and coupled to the lower surface of the outer case 12. The hanger 80 may project downward from the combined case 12 and 14 and may project forward.

The second hanger part 82 may be positioned behind the first hanger part 81 so as to be spaced apart from the first hanger part 81. The second hanger part 82 may extend horizontally at a lower portion of the hanger 80, and the opposite ends of the second hanger part 82 may be bent upward and coupled to the opposite sides of the first hanger part 81.

Towels 1 or other objects may be respectively hanged on the first hanger part 81 and the second hanger part 82. Other objects may be hung on the first hanger part 81 or the second hanger part 82, such as laundry. Although the following description discusses a towel 1 being hung on the first hanger part 81 and/or the second hanger part 82 for convenience of description, the description is applicable to other objects.

The outer case 12 may include, on the lower surface thereof, a first sensor 86 to detect the presence of a towel 1 hanging on the first hanger part 81 or the second hanger part 82. In addition, each of the first hanger part 81 and the second hanger part 82 may be provided with a second sensor 87 to detect moisture in the towel 1. The first sensor 86 may be an ultrasonic sensor, and the second sensor 87 may be an electrode sensor. The first sensor 86 may detect the presence of a towel 1 hanging on the first hanger part 81 or the second hanger part 82 and may output a first signal value when a towel 1 is hanging on the first hanger part 81 or the second hanger part 82. The second sensor 87 may detect moisture in a towel 1 hanging on the first hanger part 81 or the second hanger part 82 and may output a second signal value when moisture is detected (or when the detected moisture levels exceed a prescribed level).

Control of the bathroom management apparatus 100 for drying and sterilizing a towel 1 hanging on the first hanger part 81 or the second hanger part 82 will now be briefly described. The first signal value that is output from the first sensor 86 may be input to the controller 90, and the second signal value that is output from the second sensor 87 may be input to the controller 90.

When the first signal value is input to the controller 90, the controller 90 may determine that a towel 1 is hanging on at least one of the first hanger part 81 or the second hanger part 82 and may compare the second signal value with a setting value. When the second signal value is equal to or higher than the setting value, the controller 90 may activate the intake vane motor 200 so as to open the intake vane 220, activate the motor 700 so as to allow an airflow between the main flow channel 31 and the second sub flow channel 33 via the flow-channel-changing damper 35 and so as to open the second air discharge port 12a via the second discharge vane 26, and activate the blower fan 40 and the heater so as to dry the towel 1.

Thereafter, when the second signal value becomes lower than the setting value, the controller 90 may determine that drying of the towel 1 is completed and may activate the ionizers 70 so as to sterilize the towel 1. When the towel becomes damp again, the procedure of drying the towel 1 may continue by activating the heater 50 until the second signal value again becomes lower than the setting value. When the second signal value again becomes lower than the setting value, the controller 90 may determine that drying of the towel 1 is recompleted, and may reactivate the ionizers 70 so as to sterilize the towel 1.

Thereafter, when a predetermined period of time elapses, the controller 90 may determine that sterilization of the towel 1 is completed. Specifically, when the ionizers 70 have been activated for a predetermined period of time, the controller 90 may determine that sterilization of the towel is completed. Accordingly, the controller 90 may halt the blower fan 40, the heater 50 and the ionizers 70, may activate the intake vane motor 200 so as to close the intake vane 22, and activate the motor 700 so as not only to block the air path between the main flow channel 31 and the second sub flow channel 33 through the flow-channel-changing damper 35 but also to close the second air discharge port 12a by closing the second discharge vane 26.

The hanger 80 may be provided with projecting hanger parts (or hanger projections) 85, which may project rearward. Since the bathroom management apparatus 100 is installed on a side wall of a bathroom, the projecting hanger parts 85 may preferably project forward rather than projecting rearward. The projecting hanger parts 85 may project rearward from the first hanger part 81. However, the projecting hanger parts 85 are not limited to the embodiment in which they project rearward from the first hanger part 81, and may project rearward from opposite sides of the hanger 80. Objects other than a towel 1 (for example, a handle of a cup) may be hung on the projecting hanger parts 85.

A towel 1 or other kind of object hanging on the hanger 80 may be efficiently dried and sterilized by air discharged through the second air discharge port 12a. The installation position of the hanger 80, which enables a towel 1 or other object to be efficiently dried and sterilized by the air discharged through the second air discharge port 12a, will now be described.

Figure 27:
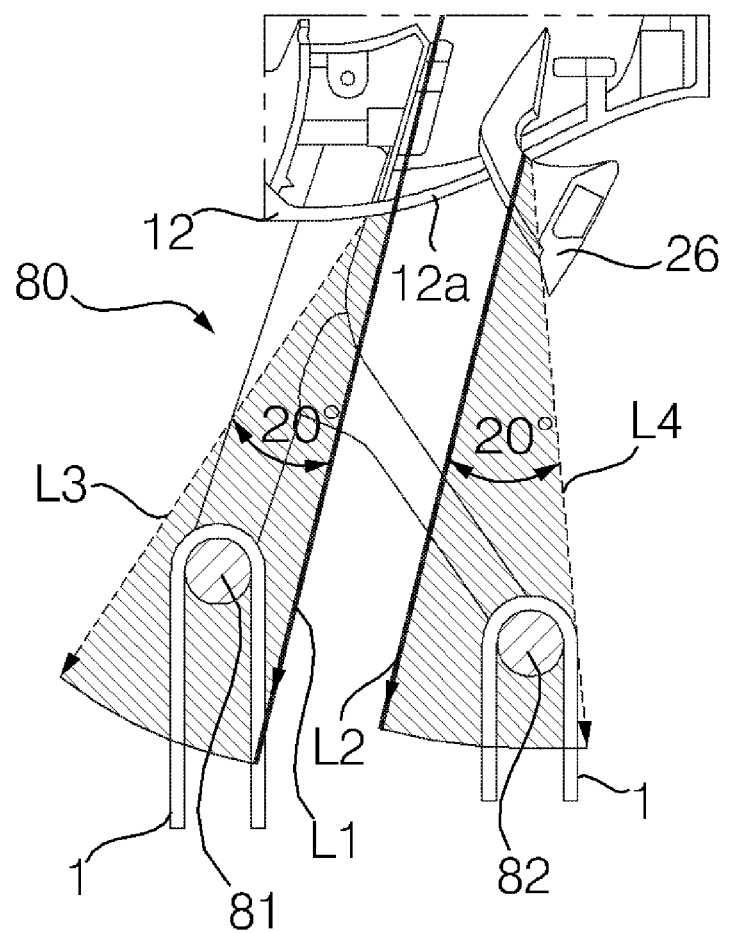
FIG. 27 is a view illustrating the installation position of the hanger.

FIG. 27 is a view illustrating an installation position of the hanger. Referring to FIG. 27, when the second air discharge port 12a is opened, the front end of the second discharge vane 26 may be positioned behind and under the second air discharge port 12a.

The first hanger part 81 may be positioned between a first tangential line L1 that extends along the front inner surface of the second air discharge port 12a and a first straight line L3 obtained by rotating the first tangential line L1 about a lower front end of the second air discharge port 12a to a predetermined angle.

The predetermined angle may also be the angle defined between a second tangential line L2 that extends along a rear inner surface of the second air discharge port 12a and a second straight line L4 that extends through a lower rear end of the second air discharge port 12a and the front end of the opened second discharge vane 26. In one embodiment, the predetermined angle is set to be 20 degrees.

The second hanger part 82 may be provided between the second tangential line L2 and the second straight line L4.

The second hanger part 82 may be positioned at a level lower than the level of the first hanger part 81, or the second hanger part 82 may be positioned at the same level as the level of the second first hanger part 81. When the second hanger part 82 is positioned at a level higher than that of the first hanger part 81, some of the air discharged from the second air discharge port 12a may not be transferred to the towel 1 hanging on the second hanger part 82 because the second hanger part 82 is positioned behind the second straight line L4 (i.e. out of the flow of air). Accordingly, it may be preferable that the second hanger part 82 be positioned at a level equal to or lower than a level of the first hanger part 81.

Although the projecting hanger parts 85 are described as being formed at the hanger 80 in the above disclosure, projecting hanger parts 900 may be mounted on the lower surface of the combined case 12 and 14 so as to enable various kinds of objects to be hanged thereon. The projecting hanger parts 900 will now be described.

Figure 14:
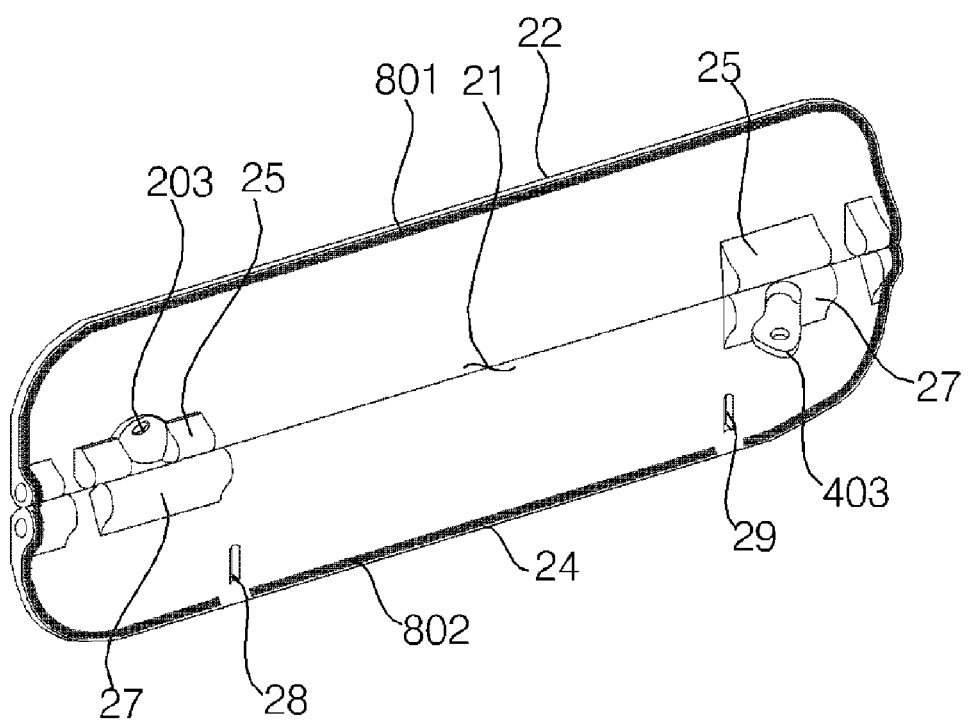
FIG. 14 is a rear perspective view illustrating the intake vane and the first discharge vane of the bathroom management apparatus according to the embodiment of the present disclosure.
Figure 15:
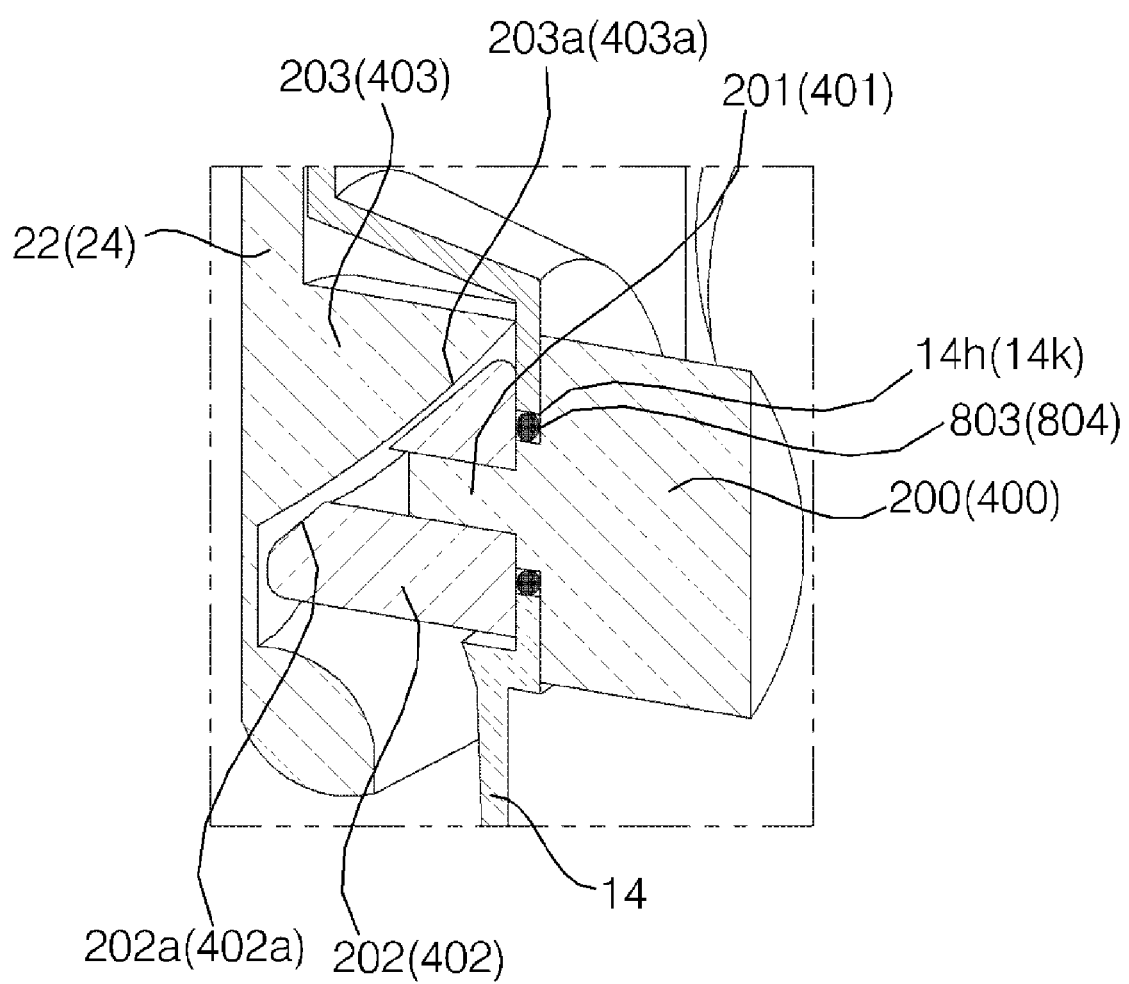
FIG. 15 is a perspective view showing a partial section of the embodiment of the present disclosure, in which the intake vane and the first discharge vane are closed.
Figure 16:
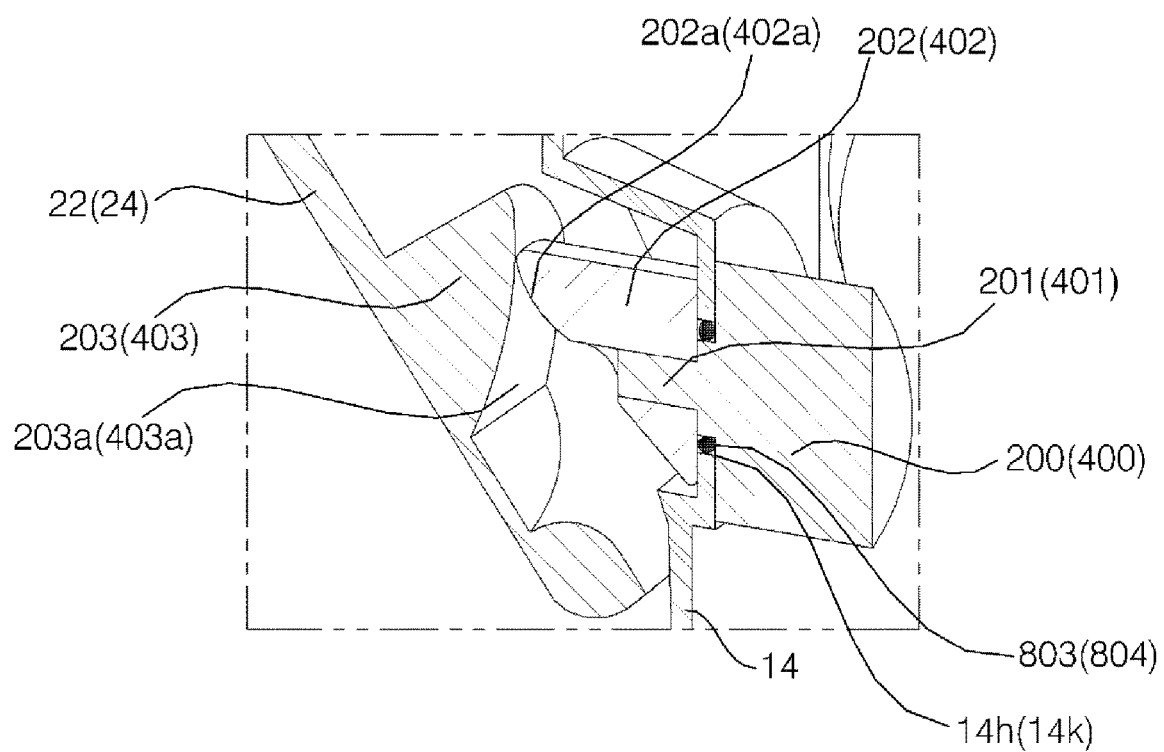
FIG. 16 is a perspective view showing a partial section of the embodiment of the present disclosure, in which the intake vane and the first discharge vane are opened.
Figure 17:
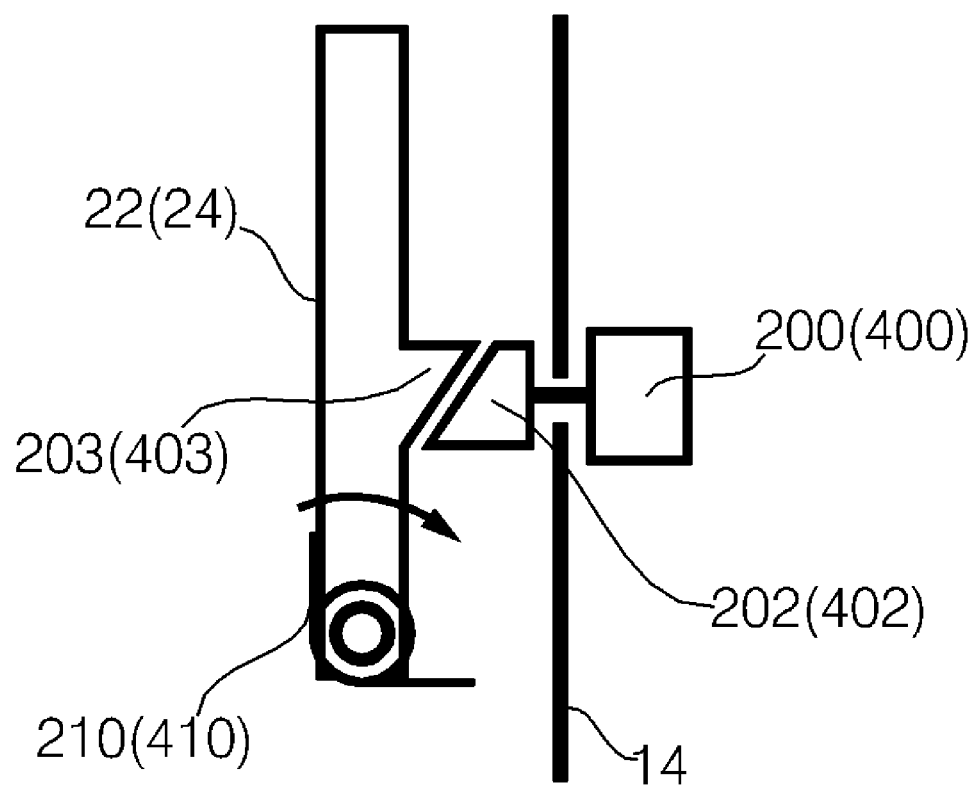
FIG. 17 is a side cross-sectional view of the embodiment of the present disclosure, in which the intake vane and the first discharge vane are closed.
Figure 18:
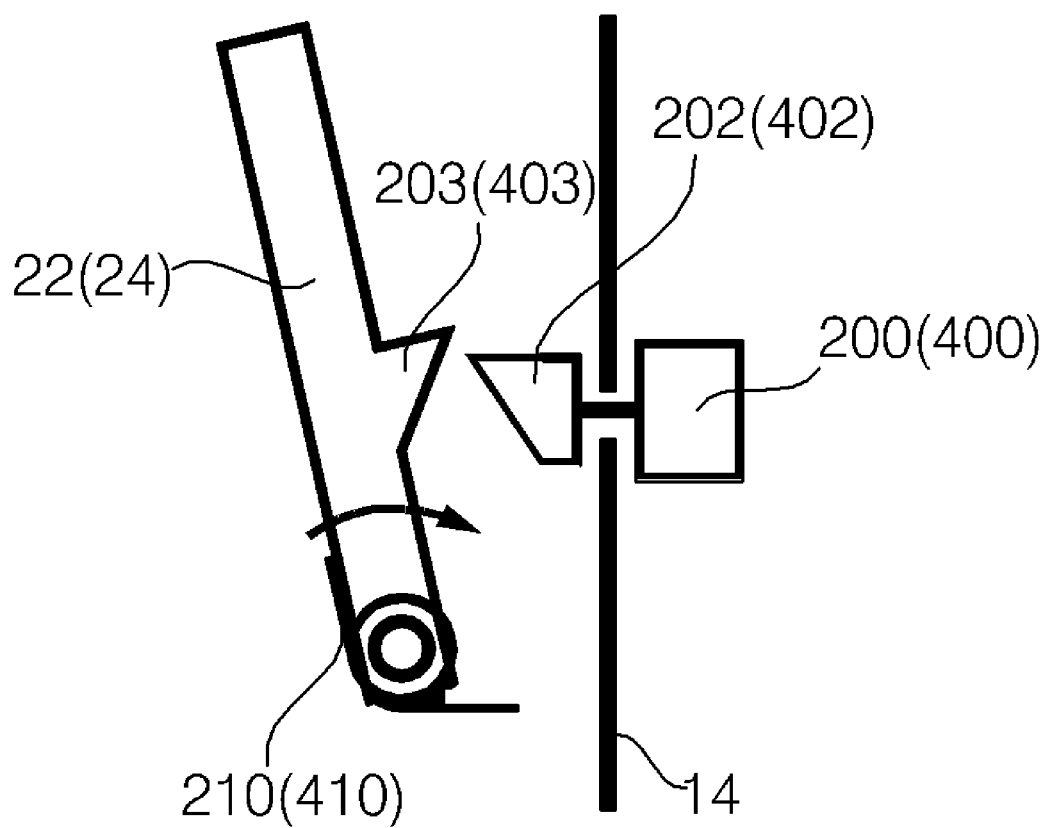
FIG. 18 is a side cross-sectional view of the embodiment of the present disclosure, in which the intake vane and the first discharge vane are opened.
Figure 19:
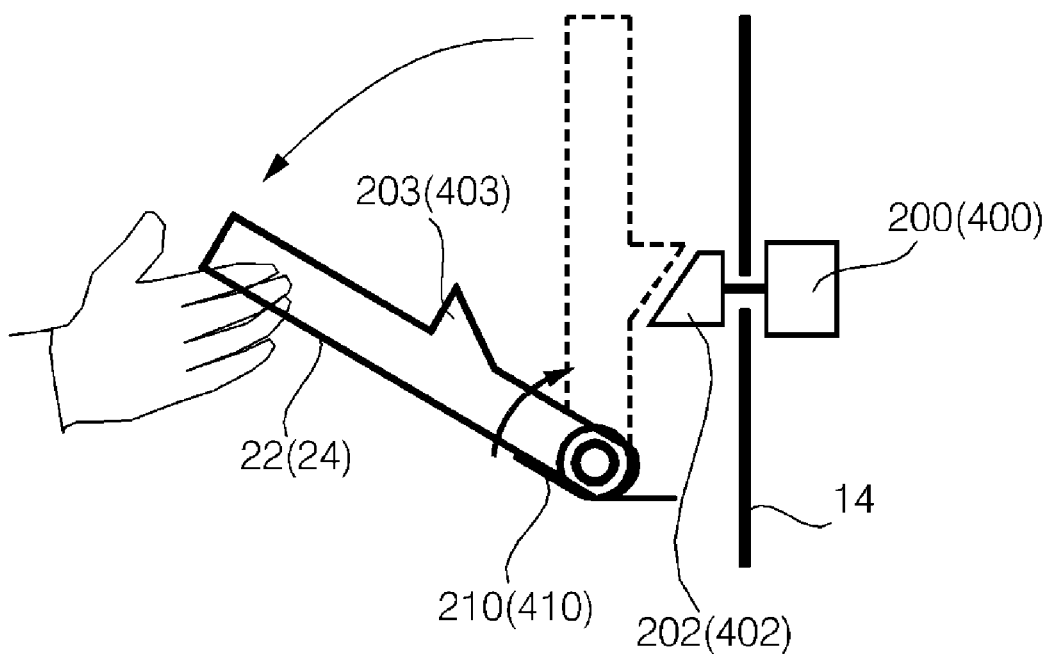
FIG. 19 is a side cross-sectional view of the embodiment of the present disclosure, in which the intake vane and the first discharge vane are opened by a user.
Figure 28:
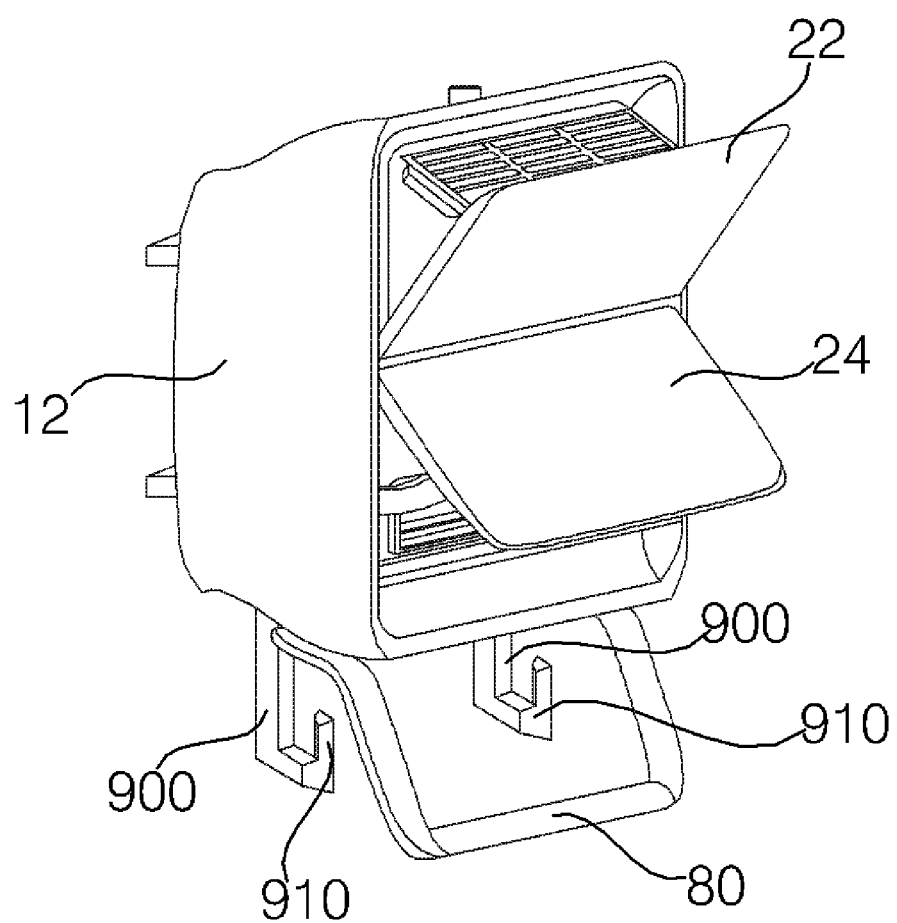
FIG. 28 is a view illustrating a hanger and projecting hangers, which have different structures.
Figure 29:
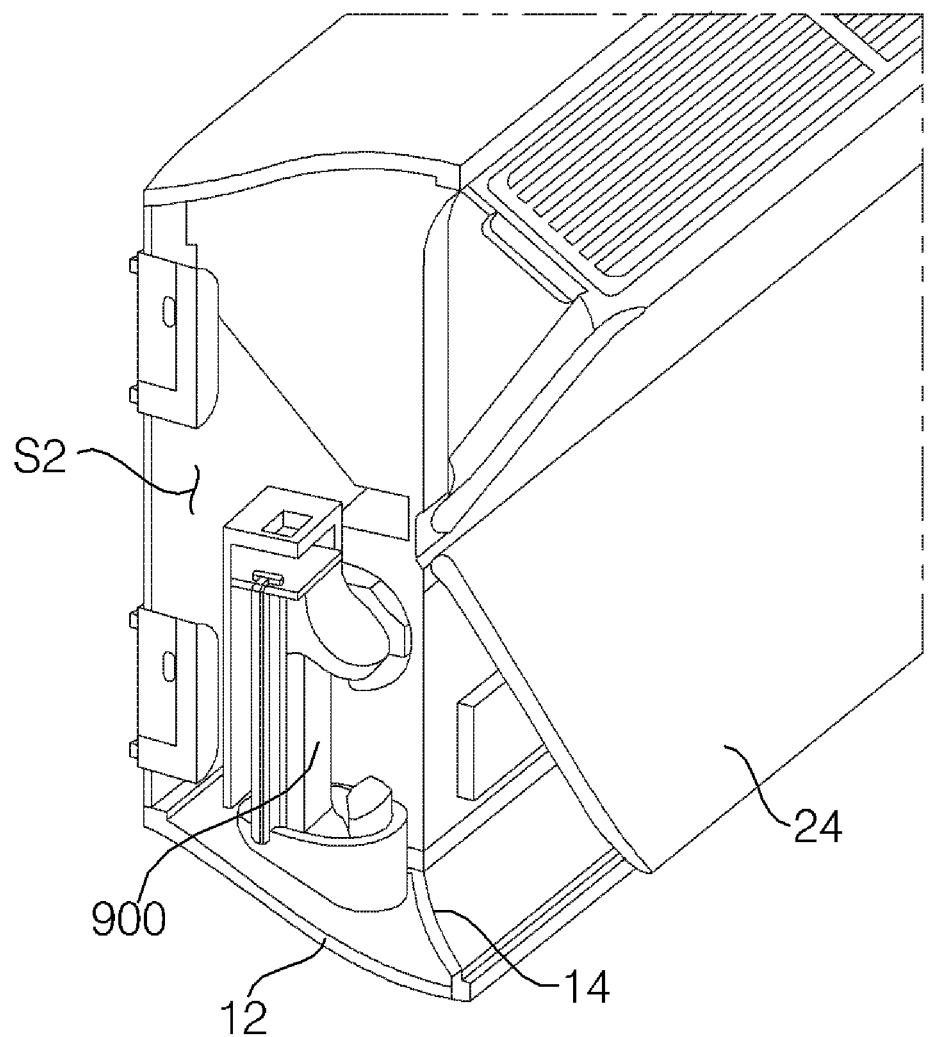
FIG. 29 is a view illustrating the projecting hangers received in the case.
Figure 30:
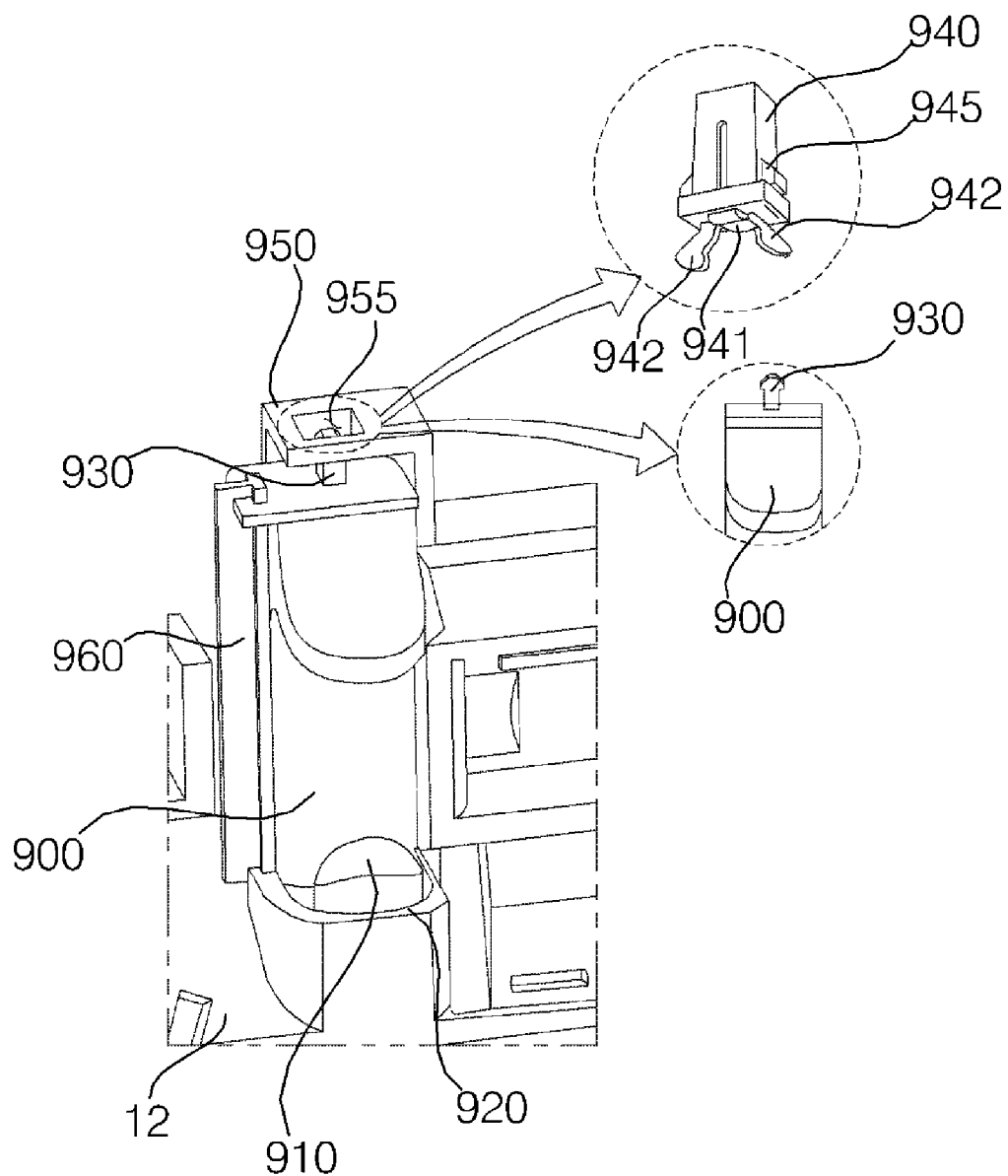
FIG. 30 is a view illustrating a latch, which includes enlarged views of substantial parts of FIG. 29.

Referring to FIGS. 14, 28 and 30, the projecting hangers 900, which may slide onto the combined case 12 and 14 and project downward from the combined case 12 and 14, may be provided behind the hanger 80. The projecting hangers 900 may include, at the lower end thereof, projecting hanger parts 910. Each of the projecting hanger parts 910 may be configured to have a hook shape. The bathroom management apparatus 100 may include two projecting hangers 900, which may be respectively received in the first and second electric component compartments S1 and S2. The hangers 900 may be inserted into the combined case 12 and 14, and when a user pushes the lower end of the projecting hanger 900 upward the projecting hanger 900 may drop to project downward from the outer case 12.

In some cases, a single projecting hanger 900 may be provided in only one of the first and second electric component compartments S1 and S2. The region of the lower surface of the combined case 12 and 14 that corresponds to at least one of the first and second electric component compartments S1 and S2 may be provided with an entrance hole 920 through which the projecting hanger 900 may be projected and retracted.

The projecting hanger 900 may include, on the upper surface thereof, a holding protrusion 930, and the combined case 12 and 14 may include a latch 940, which holds or releases the holding protrusion 930 in response to a user's action of pushing the projecting hanger 900.

The region of the rear surface of the inner case 14 that corresponds to the one of the first and second electric component compartments S1 and S2 that accommodates the projecting hanger 900 is may have a latch attachment 950. The latch attachment 950 may include a fitting hole 955 through which the latch 940 passes. The fitting hole 955 may be provided above the entrance hole 920.

The latch 940 may include, on the opposite lateral sides thereof, hooks 945. Accordingly, when the latch 940 is fitted into the fitting hole 955 from below and the hooks 945 are engaged with the upper surface of the latch attachment 950, the latch 940 may be coupled to the latch attachment 950.

The latch 940 may include, at the center of the lower end thereof, a push portion 941, which may be pushed by the holding protrusion 930. Holding portions may be provided at opposite sides of the push portion 941. The holding portions 942 may be repeatedly closed and spread so as to hold and release the holding protrusion 930 each time the push portion 941 is pushed by the holding protrusion 930.

When a user pushes the lower end of the projecting hanger 900 upward through the entry hole 920 formed in the lower end of the outer case 12 while the projecting hanger 900 is received in the combined case 12 and 14, the holding protrusion 930 may move the push portion 941 so as to spread the two holding portions 942 outward, thereby releasing the holding protrusion 930 from the engagement with the holding portions 942. Therefore, the projecting hanger 900 may slide downward and may be projected downward from the outer case 12 through the entry hole 920.

When a user inserts the projecting hanger 900, which is projecting outward from the combined case 12 and 14, into the combined case 12 and 14 and then once again pushes the lower end of the projecting hanger 900 upward through the entry hole 920, the holding protrusion 930 may push the push portion 941 so as to close the two holding portions 942, thereby causing the holding protrusion 930 to be held between the holding portions 942. Therefore, the projecting hanger 900 may be maintained in the state of being received in the combined case 12 and 14. The combined case 12 and 14 may include a guide 960 to guide the vertical sliding movement of the projecting hanger 900.

As described above, since the bathroom management apparatus 100 according to the embodiment of the present disclosure may be provided with the hanger 80 at an optimal installation position, objects hanging on the hanger 80 may be more efficiently dried and sterilized.

In addition, since the hanger 80 may be further provided with the projecting hanger parts 85 or the separate projecting hangers 900, it is also possible to hang various kinds of objects other than a towel 1 on the hanger 80.

The bathroom management apparatus may be provided with the hanger, which is positioned at an optimal installation position to efficiently dry and sterilize objects hanging on the hanger. The projecting hanger parts may be integrally formed at the hanger and it is possible to hang objects such as cups on the projecting hanger parts. A user can extend the project hanger from the case for use thereof when necessary, and can store the projecting hanger in the case when not needed. The bathroom management apparatus can be automatically operated so as to dry objects hanging on the hanger when the objects are wet, and can be automatically stopped when the objects are dried.

Aspects of the present disclosure provide a bathroom management apparatus including a hanger, which is provided at an optimal installation position so as to efficiently dry and sterilize objects hanging on the hanger. Aspects the present disclosure provide a bathroom management apparatus including projecting hanger parts integrally formed at the hanger. Aspects of the present disclosure provide a bathroom management apparatus including a projecting hanger, which is able to project or extend from the case when necessary, and is able to be stored in the case when not need. Aspects of the present disclosure provide a bathroom management apparatus, which can be automatically operated or stopped in response to the detection of moisture in objects hanging on the hanger.

A bathroom management apparatus according to an embodiment the present disclosure includes a case including a second air discharge port formed in a lower surface thereof so as to allow air to be discharged through the second air discharge port, a second discharge vane for opening and closing the second air discharge port, and a hanger coupled to the lower surface of the case and including a first hanger part formed thereon, wherein a front end of the second discharge vane is positioned behind and under the second air discharge port when the second air discharge port is opened, wherein the first hanger part is positioned between a first tangential line that extends along a front inner surface of the second air discharge port and a first straight line obtained by rotating the first tangential line about a lower front end of the second air discharge port to a predetermined angle, and wherein the predetermined angle is an angle defined between a second tangential line that extends along a rear inner surface of the second air discharge port and a second straight line that extends through a lower rear end of the second air discharge port and a front end of the opened second discharge vane.

In certain embodiments, the case may further include an air intake port formed in a front surface thereof, and the bathroom management apparatus further includes an intake vane motor for driving an intake vane for opening and closing the air intake port, a motor for driving the second discharge vane, a blower fan for sucking air through the air intake port and blowing the air toward the second air discharge port, a heater for heating air, which is blown toward the second air discharge port by the blower fan, a first sensor for detecting an object hanging on the first hanger part and outputting a first signal value, a second sensor for detecting moisture in an object hanging on the first hanger part and outputting a second signal value, and a controller for driving the intake vane motor so as to open the intake vane, driving the motor so as to open the second discharge vane and driving the blower fan and the heater when the first signal value is input and the second signal value is equal to or higher than a setting value.

Any reference in this specification to "one embodiment," "an embodiment," "example embodiment," etc., means that a particular feature, structure, or characteristic described in connection with the embodiment is included in at least one embodiment of the disclosure. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bathroom management apparatus comprising:
   a case including a air discharge port formed in a lower surface thereof so as to allow air to be discharged through the air discharge port;
   a discharge vane configured to move to selectively cover or expose the air discharge port; and
   a hanger coupled to the lower surface of the case and including a first hanger cylinder,
   wherein the first hanger cylinder is positioned between a first tangential line that extends along a front inner surface of the air discharge port and a first straight line obtained by rotating the first tangential line about a lower front end of the air discharge port to a predetermined angle, and
   wherein the predetermined angle corresponds to an angle defined between a second tangential line that extends along a rear inner surface of the air discharge port and a second straight line that extends through a lower rear end of the air discharge port and a front end of the discharge vane when moved to expose the air discharge port.

2. The bathroom management apparatus according to claim 1, wherein the hanger further includes a hanger projection extending rearward therefrom.

3. The bathroom management apparatus according to claim 1, wherein the bathroom management apparatus is mounted to a vertical surface,
   wherein the hanger further includes a hanger cylinder, which is spaced apart from and is between the first hanger cylinder and the vertical surface, and
   wherein the hanger cylinder is positioned between the second tangential line and the second straight line.

4. The bathroom management apparatus according to claim 3, wherein the second hanger cylinder is positioned vertically further from the lower surface of the case than the first hanger cylinder.

5. The bathroom management apparatus according to claim 3, wherein the second hanger cylinder and the first hanger cylinder are positioned a same vertical distance from the lower surface of the case.

6. The bathroom management apparatus according to claim 1, further comprising a projecting hanger, which configured to be slidably inserted into or move out of the case so as to project downward from the case when moved out of the case, and the projecting hanger including a projecting hanger extension.

7. The bathroom management apparatus according to claim 6, wherein the air discharge port is a second air discharge port and the discharge vane is a second discharge vane,
   wherein the case further includes an air intake port formed in an upper region of a front surface thereof and a first air discharge port formed in a lower region of the front surface,
   wherein the bathroom management apparatus further comprises a duct, which is provided in the case so as to allow the air intake port, the first air discharge port and the second air discharge port to communicate with each other,
   wherein the case includes a first electric component compartment formed at one lateral side of the duct and a second electric component compartment formed at another lateral side of the duct, and
   wherein the case includes an entry hole formed in a region of the lower surface of the case that corresponds to at least one of the first or the second electric component compartments through which the projecting hanger passes.

8. The bathroom management apparatus according to claim 6, wherein the projecting hanger includes a holding protrusion formed on a upper surface thereof, and
   wherein the bathroom management apparatus further comprises a latch, which is internally coupled to the case so as to selectively hold or release the holding protrusion in response to a user pushing the projecting hanger.

9. The bathroom management apparatus according to claim 8, wherein the case includes a latch attachment having a fitting hole into which the latch is fitted, and
   wherein the latch includes a hook, which is engaged with the latch attachment.

10. The bathroom management apparatus according to claim 6, further comprising a guide provided in the case so as to guide vertical sliding movement of the projecting hanger.

11. The bathroom management apparatus according to claim 1, wherein the air discharge port is a second air discharge port and the discharge vane is a second discharge vane,
wherein the case further includes an air intake port formed in an upper region of a front surface thereof and an first air discharge port formed in a lower region of the front surface, and
wherein the bathroom management apparatus further comprises:
a duct provided in the case so as to allow the air intake port, the first air discharge port and the air discharge port to communicate with each other, and
a blower fan provided in the duct so as to suck air through the air intake port and blow the air toward at least one of the first air discharge port or the second air discharge port.

12. The bathroom management apparatus according to claim 11, further comprising:
an intake vane that moves to selectively cover or expose the air intake port; and
a first discharge vane that moves to selectively cover or expose the first air discharge port.

13. The bathroom management apparatus according to claim 11, further comprising a heater provided in the duct so as to heat air in the duct.

14. The bathroom management apparatus according to claim 11, further comprising an ionizer provided in the duct so as to generate ions released into the air in the duct.

15. The bathroom management apparatus according to claim 11, further comprising a filter provided in the air intake port.

16. The bathroom management apparatus according to claim 15, further comprising;
a lighting source configured to emit light; and
a reflector provided on a rear surface of the intake vane to reflect the light from the lighting source toward the filter.

17. The bathroom management apparatus according to claim 15, further comprising a lighting source configured to emit light toward the filter.

18. The bathroom management apparatus according to claim 11, further comprising a damper provided in the duct so as to selectively direct air in the duct through the air intake port toward one of the first air discharge port or the second air discharge port.

19. The bathroom management apparatus according to claim 1, wherein the case further includes an air intake port formed in a front surface thereof, and
wherein the bathroom management apparatus further comprises:
an intake vane motor configured to move an intake vane to selectively cover or expose the air intake port;
a motor configured to move the discharge vane;
a blower fan configured to suck in air through the air intake port and to blow the air toward the air discharge port;
a heater configured to heat the air being blown toward the air discharge port by the blower fan;
a first sensor configured to detect whether an object is hanging on the hanger and to output a first signal value when the object is hanging on the hanger;
a second sensor configured to detect an amount of moisture in the object hanging on the hanger and outputting a second signal value associated with the detected amount of moisture; and
a controller that is configured to activate the intake vane motor so as to move the intake vane to expose the air intake port, activate the motor so as to move the discharge vane to expose the air discharge port, and activate the blower fan and the heater when the first signal value is received from the first sensor and the second signal value indicates that the amount of moisture is equal to or higher than a setting value.

20. The bathroom management apparatus according to claim 19, further comprising an ionizer configured to generate ions and to provide the ions to the air blown toward the air discharge port by the blower fan, and
wherein the controller is further configured to activate the ionizer when the second signal value becomes lower than the setting value.

* * * * *